(12) United States Patent
Tange et al.

(10) Patent No.: US 11,395,798 B2
(45) Date of Patent: Jul. 26, 2022

(54) O/W TYPE EMULSION

(71) Applicants: NOF CORPORATION, Tokyo (JP); NATIONAL UNIVERSITY CORPORATION HOKKAIDO UNIVERSITY, Sapporo (JP)

(72) Inventors: Kota Tange, Kawasaki (JP); Yuta Nakai, Kawasaki (JP); Hidetaka Akita, Sapporo (JP); Hiroki Tanaka, Sapporo (JP); Ayaka Watanabe, Sapporo (JP); Naoya Miura, Sapporo (JP); Hideyoshi Harashima, Sapporo (JP)

(73) Assignees: NOF CORPORATION, Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 639 days.

(21) Appl. No.: 15/765,900

(22) PCT Filed: Jun. 29, 2016

(86) PCT No.: PCT/JP2016/069358
§ 371 (c)(1),
(2) Date: Apr. 4, 2018

(87) PCT Pub. No.: WO2017/061150
PCT Pub. Date: Apr. 13, 2017

(65) Prior Publication Data
US 2019/0110986 A1 Apr. 18, 2019

(30) Foreign Application Priority Data
Oct. 8, 2015 (JP) .............................. JP2015-200148

(51) Int. Cl.
| A61K 9/107 | (2006.01) |
| A61K 47/20 | (2006.01) |
| A61K 47/22 | (2006.01) |
| A61K 31/37 | (2006.01) |
| A61K 31/573 | (2006.01) |
| A61K 31/575 | (2006.01) |
| A61K 47/24 | (2006.01) |
| A61K 47/28 | (2006.01) |

(52) U.S. Cl.
CPC ............ *A61K 9/107* (2013.01); *A61K 9/1075* (2013.01); *A61K 31/37* (2013.01); *A61K 31/573* (2013.01); *A61K 31/575* (2013.01); *A61K 47/20* (2013.01); *A61K 47/22* (2013.01); *A61K 47/24* (2013.01); *A61K 47/28* (2013.01)

(58) Field of Classification Search
CPC .... A61K 9/107; A61K 9/1075; A61K 31/575; A61K 47/20; A61K 47/22; A61K 31/37; A61K 31/573; A61K 47/24; A61K 47/28; A61P 37/06; A61P 3/06; A61P 35/00; A61P 31/10; A61P 31/04; A61P 31/00; A61P 29/00
See application file for complete search history.

(56) References Cited

U.S. PATENT DOCUMENTS 6,623,765 B1    9/2003 Dennis et al.
2003/0040497 A1* 2/2003 Teng .................... A61K 48/00
                                                      514/44 R
(Continued)

FOREIGN PATENT DOCUMENTS

CN    103315954 A    9/2013
CN    103930398 A    7/2014
(Continued)

OTHER PUBLICATIONS

Akita et al., "Molecular Tuning of a Vitamin E-Scaffold pH-Sensitive and Reductive Cleavable Lipid-like Material for Accelerated in Vivo Hepatic siRNA Delivery," *ACS Biomater. Sci. Eng.*, 1(9): 834-844 (2015).
(Continued)

*Primary Examiner* — Matthew P Coughlin
*Assistant Examiner* — Thurman Wheeler
(74) *Attorney, Agent, or Firm* — Leydig, Voit & Mayer, Ltd.

(57) ABSTRACT

The present invention provides an O/W type emulsion having a volume median diameter of not more than 100 nm and containing a compound represented by the formula (1)

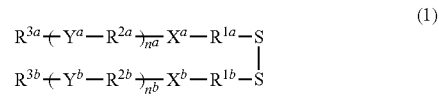

(1)

wherein $X^a$ and $X^b$ are each independently $X^1$, $X^2$ or a 1,4-piperazinediyl group;

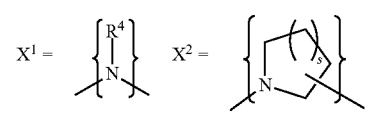

s is 1 or 2,
$R^4$ is an alkyl group having 1-6 carbon atoms,
$n^a$ and $n^b$ are each independently 0 or 1,
$R^{1a}$, $R^{1b}$, $R^{2a}$ and $R^{2b}$ are each independently an alkylene group having 1-6 carbon atoms,
$Y^a$ and $Y^b$ are each independently an ester bond, or the like, and
$R^{3a}$ and $R^{3b}$ are each independently a liposoluble vitamin residue or the like.

10 Claims, 12 Drawing Sheets

(56) References Cited

U.S. PATENT DOCUMENTS

| | | | | |
|---|---|---|---|---|
| 2008/0274195 A1* | 11/2008 | Nicolosi | ............... | A61P 3/06 424/489 |
| 2010/0305218 A1* | 12/2010 | Wooster | ............... | A61K 47/14 514/784 |
| 2014/0335157 A1* | 11/2014 | Tange | ............... | A61K 47/22 424/450 |
| 2015/0335574 A1 | 11/2015 | Nicolos et al. | | |

FOREIGN PATENT DOCUMENTS

| | | |
|---|---|---|
| JP | 2004-505033 A | 2/2004 |
| JP | 2009-501802 A | 1/2009 |
| JP | 2011-505235 A | 2/2011 |
| WO | WO 2013/073480 A1 | 5/2013 |

OTHER PUBLICATIONS

Akita et al., "A Neutral Envelope-Type Nanoparticle Containing pH-Responsive and SS-Cleavable Lipid-Like Material as a Carrier for Plasmid DNA," *Adv. Healthcare Mater.*, 2(8): 1120-1125 (2013).

Cabral et al., "Accumulation of sub-100 nm polymeric micelles in poorly permeable tumours depends on size," *Nat. Nanotechnol.*, 6(12): 815-823 (2011).

Klibanov et al., "Activity of amphipathic poly(ethylene glycol) 5000 to prolong the circulation time of liposomes depends on the liposome size and is unfavorable for immunoliposome binding to target," *Biochim. Biophys. Acta*, 1062(2): 142-148 (1991).

Litzinger et al., "Effect of liposome size on the circulation time and intraorgan distribution of amphipathic poly(ethylene glycol)-containing liposomes," *Biochim. Biophys. Acta*, 1190(1): 99-107 (1994).

Tanaka et al., "Neutral biodegradable lipid-envelope-type nanoparticle using vitamin A-Scaffold for nuclear targeting of plasmid DNA," *Biomaterials*, 35(5): 1755-1761 (2014).

Japanese Patent Office, International Search Report in International Patent Application No. PCT/JP2016/069358 (dated Sep. 6, 2016).

Yangming, "Pharmaceutics," China Medical Science and Technology Press, pp. 234-238 (Aug. 31, 2014).

China National Intellectual Property Administration, First Office Action in Chinese Patent Application No. 201680058794.4 (dated Jun. 29, 2020).

* cited by examiner

O/W TYPE EMULSION

CROSS-REFERENCE TO RELATED APPLICATIONS

This patent application is the U.S. national phase of International Patent Application No. PCT/JP2016/069358, filed on Jun. 29, 2016, which claims the benefit of Japanese Patent Application No. 2015-200148, filed on Oct. 8, 2015, which are incorporated by reference in their entireties herein.

TECHNICAL FIELD

The present invention relates to an O/W type emulsion disintegratable in response to the reductive environment in the cells and a preparation method thereof. In addition, the present invention relates to use of the O/W type emulsion as a carrier for delivering a hardly water-soluble drug into the cells.

BACKGROUND ART

Most of the candidate substances of new drugs such as antineoplastic drug, immunosuppressant, antibiotic, antifungal agent, antilipemic, anti-inflammatory agent and the like are hardly water-soluble. Even when they have sufficient pharmacological activities, the development is often withheld or ceased due to the difficulty in formulating them.

Conventionally, when applying a hardly water-soluble drug to a pharmaceutical product, attempts have been made such as solubilization with a hydrophilic surfactant or a clathrate compound such as cyclodextrin, or emulsification using vegetable oil and lecithin. To achieve desired efficacy while reducing side effects, it is further necessary to control average particle size and promote release in the cell so that accumulation in the object cells and tissues can be enhanced.

Examples of a solubilizer with controlled average particle size include polymer micelles described in non-patent document 1 and liposomes described in non-patent document 2 and non-patent document 3. These documents teach that they are advantageous for administration to the body because an average particle size controlled to 100 nm or below makes it possible to increase retentivity in blood by avoiding discharge from the spleen and enhance accumulation in the target tissue such as tumor or the like. However, these micelles and liposomes have room for improvement in terms of efficiency of drug release in cells.

The present inventors have developed lipids having properties to disintegrate a lipid membrane structure in the cell (patent document 1, patent document 2). Lipid structures such as liposome and the like containing the lipids are easily disintegrated under reduction environment in the cell and release a nucleic acid, which is a water-soluble compound, with high efficiency. Therefore, the lipid structures can be used as superior carriers for efficiently delivering nucleic acid into the cell.

DOCUMENT LIST

Patent Documents patent document 1: WO 2013/073480
patent document 2: US 20140335157

Non-Patent Document non-patent document 1: Nat Nanotechnol. 2011 Oct. 23; 6(12):815-23. Accumulation of sub-100 nm polymeric micelles in poorly permeable tumours depends on size. Cabral H, Matsumoto Y, Mizuno K, Chen Q, Murakami M, Kimura M, Terada Y, Kano M R, Miyazono K, Uesaka M, Nishiyama N, Kataoka K.
non-patent document 2: Biochimica et Biophysica Acta, 1062 (1991) 142-148Activity of amphipathic poly(ethylene glycol) 5000 to prolong the circulation time of liposomes depends on the liposome size and is unfavorable for immunoliposome binding to target. Aleksander L. Klibanov, Kazuo Maruyama, Anne Marie Beckerleg, Vladimir P. Torchilin and Leaf Huang
non-patent document 3: Biochimica et Biophysica Acta 1190 (1994) 99-107Effect of liposome size on the circulation time and intraorgan distribution of amphipathic poly(ethylene glycol)-containing liposomes. David C. Litzinger, Antoinette M. J. Buiting, Nico van Rooijen, and Leaf Huang

SUMMARY OF THE INVENTION

Problems to be Solved by the Invention

The present invention aims to provide a carrier for efficiently delivering hardly water-soluble drugs into cells.

Means of Solving the Problems

The present inventors tried to encapsulate a hardly water-soluble drug instead of nucleic acid in liposomes containing the lipids disclosed in patent document 1 and 2 and introduce same into cells. However, they failed to produce the liposome stably encapsulating the hardly water-soluble drug. It was also difficult to control the particle size of the liposome to 100 nm or below which is advantageous for administration to the body. The present inventors further continued trials and errors and found that an O/W type emulsion prepared using the lipids disclosed in patent documents 1 and 2 as a constituent component can, unlike liposomes, stably encapsulate a hardly water-soluble drug and release the drug efficiently in response to the intracellular reductive environment. Furthermore, they have found that the volume median diameter of the O/W type emulsion can be controlled to 100 nm or below, which is advantageous for accumulation in a deep part of tissues such as tumor and the like when administered to the body, by preparing the O/W type emulsion under particular conditions, which resulted in the completion of the present invention.

Accordingly, the present invention encompasses the following.

[1] An O/W type emulsion having a volume median diameter of not more than 100 nm and comprising a compound represented by the formula (1)

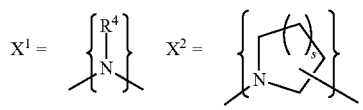

wherein $X^a$ and $X^b$ are each independently $X^1$, $X^2$ or 1,4-piperazinediyl group;

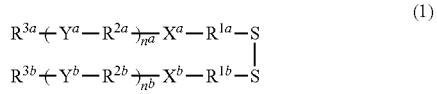

(1)

s is 1 or 2,
R$^4$ is an alkyl group having 1-6 carbon atoms,
n$^a$ and n$^b$ are each independently 0 or 1,
R$^{1a}$ and R$^{1b}$ are each independently an alkylene group having 1-6 carbon atoms,
R$^{2a}$ and R$^{2b}$ are each independently an alkylene group having 1-6 carbon atoms,
Y$^a$ and Y$^b$ are each independently an ester bond, an amide bond, a carbamate bond, an ether bond or a urea bond, and
R$^{3a}$ and R$^{3b}$ are each independently a sterol residue, a liposoluble vitamin residue or an aliphatic hydrocarbon group having 12-23 carbon atoms, as a constituent component.

[2] The O/W type emulsion of [1], wherein the volume median diameter is 30-50 nm.

[3] The O/W type emulsion of [1] or [2], further comprising at least one selected from the group consisting of phospholipid, cholesterol and PEG lipid.

[4] The O/W type emulsion of any of [1] to [3], encapsulating a hardly water-soluble drug.

[5] The O/W type emulsion of [4], wherein the hardly water-soluble drug is 4-methylumbelliferone cholesterol hemisuccinate or dexamethasone cholesterol hemisuccinate.

[6] A carrier for delivering a hardly water-soluble drug into a cell, comprising the O/W type emulsion of any of [1] to [3].

[7] A method for delivering a hardly water-soluble drug into a cell, comprising contacting the O/W type emulsion of [4] with the cell.

[8] The method of [7], wherein the O/W type emulsion is brought into contact with the cell in vitro.

[9] The method of [7], wherein the O/W type emulsion is brought into contact with the cell by administration to the body.

[10] A method for producing the O/W type emulsion of any of [1] to [4], comprising mixing an aqueous buffer solution with pH 3.0-7.4 and salt concentration 0-0.5 M and an alcohol solution of a lipid comprising a compound of the formula (1).

Effect of the Invention

According to the O/W type emulsion of the present invention, a hardly water-soluble drug can be stably encapsulated therein. When the O/W type emulsion of the present invention encapsulating a hardly water-soluble drug is taken up by cells, the compound represented by the formula (1) is decomposed by the reductive environment in the cell to disintegrate the O/W type emulsion, whereby the hardly water-soluble drug contained therein is efficiently released in the cells. Therefore, the O/W type emulsion of the present invention is useful as a carrier for delivering a hardly water-soluble drug into cells. In addition, since the O/W type emulsion of the present invention has a volume median diameter of 100 nm or below, discharge from the spleen can be avoided, high retentivity in blood and high accumulation in the target tissue such as tumor or the like can be exhibited, and it is advantageous for delivering a hardly water-soluble drug to a target tissue in the body.

DESCRIPTION OF EMBODIMENTS

Figure 1:
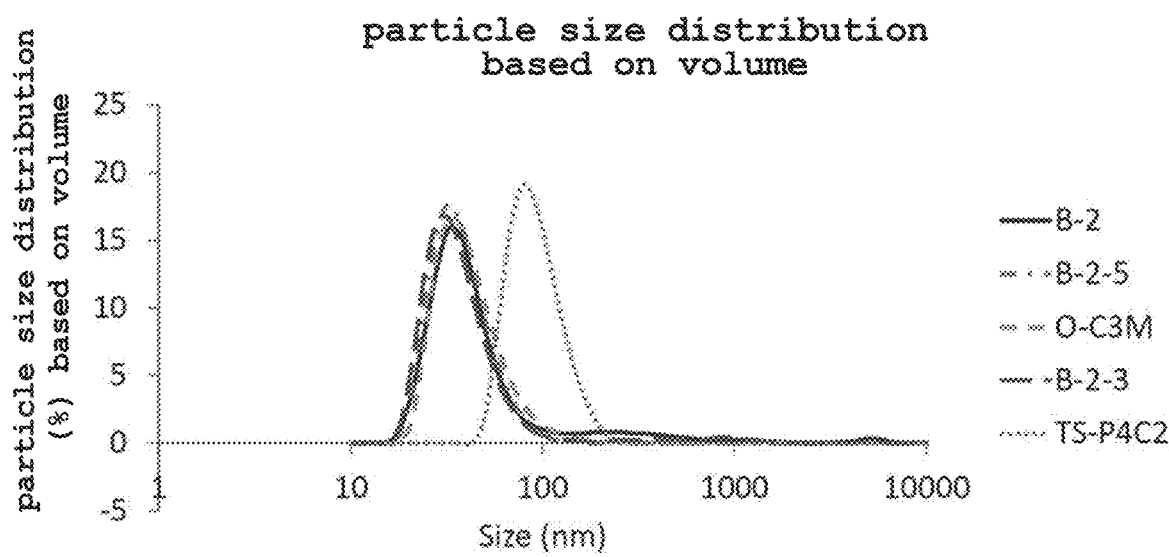
FIG. 1 shows particle size distribution based on the volume of various emulsions prepared from B-2, B-2-5, O-C3M, B-2-3 or TS-P4C2.

While the embodiments of the present invention are explained in the following, the present invention is not limited thereto.

The present invention provides an O/W type emulsion containing a compound represented by the formula (1).

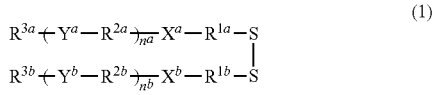

In the formula (1), $X^a$ and $X^b$ are each independently $X^1$ or $X^2$ shown below, or a 1,4-piperazinediyl group.

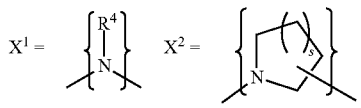

$R^4$ in $X^1$ is an alkyl group having 1-6 carbon atoms, which may be linear, branched or cyclic. The alkyl group preferably has a carbon number of 1-3. Specific examples of the alkyl group having 1-6 carbon atoms include methyl group, ethyl group, propyl group, isopropyl group, n-butyl group, sec-butyl group, isobutyl group, tert-butyl group, pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group and the like. $R^4$ is preferably a methyl group, an ethyl group, a propyl group or an isopropyl group, most preferably a methyl group.

The s in $X^2$ is 1 or 2. When s is 1, $X^2$ is a pyrrolidinium group, and when s is 2, $X^2$ is a piperidinium group. s is preferably 2. While the binding direction of $X^2$ is not limited, a nitrogen atom in $X^2$ preferably binds to $R^{1a}$ and $R^{1b}$.

$X^a$ may be the same as or different from $X^b$, and $X^a$ is preferably the same group as $X^b$.

$n^a$ and $n^b$ are each independently 0 or 1, preferably 1. When $n^a$ is 1, $R^{3a}$ binds to $X^a$ via $Y^a$ and $R^{2a}$, and when $n^a$ is 0, a structure of $R^{3a}$—$X^a$—$R^{1a}$—S— is taken. Similarly, when $n^b$ is 1, $R^{3b}$ binds to $X^b$ via $Y^b$ and $R^{2b}$, and when $n^b$ is 0, a structure of $R^{3b}$—$X^b$—$R^{1b}$—S— is taken.

$n^a$ may be the same as or different from $n^b$, and $n^a$ is preferably the same as $n^b$ $R^{1a}$ and $R^{1b}$ are each independently an alkylene group having 1-6 carbon atoms, which may be linear or branched, preferably linear. Specific examples of the alkylene group having 1-6 carbon atoms include methylene group, ethylene group, trimethylene group, isopropylene group, tetramethylene group, isobutylene group, pentamethylene group, neopentylene group and the like. $R^{1a}$ and $R^{1b}$ are each preferably a methylene group, an ethylene group, a trimethylene group, an isopropylene group or a tetramethylene group, most preferably an ethylene group.

$R^{1a}$ may be the same as or different from $R^{1b}$, and $R^{1a}$ is preferably the same group as $R^{1b}$.

$R^{2a}$ and $R^{2b}$ are each independently an alkylene group having 1-6 carbon atoms, which may be linear or branched, preferably linear. Examples of the alkylene group having 1-6 carbon atoms include those recited as the examples of the alkylene group having 1-6 carbon atoms for $R^{1a}$ or $R^{1b}$.

$R^{2a}$ and $R^{2b}$ are each preferably a methylene group, an ethylene group, a trimethylene group, an isopropylene group or a tetramethylene group.

When $X^a$ and $X^b$ are each $X^1$, $R^{2a}$ and $R^{2b}$ are each preferably a methylene group, an ethylene group, a trimethylene group, an isopropylene group or a tetramethylene group, most preferably a trimethylene group.

When $X^a$ and $X^b$ are each $X^2$, $R^{2a}$ and $R^{2b}$ are each preferably a methylene group, an ethylene group, a trimethylene group or a tetramethylene group, most preferably an ethylene group.

When $X^a$ and $X^b$ are 1,4-piperazinediyl groups, $R^{2a}$ and $R^{2b}$ are each preferably a methylene group, an ethylene group, a trimethylene group or a tetramethylene group, and most preferably an ethylene group.

$R^{2a}$ may be the same as or different from $R^{2b}$, and $R^{2a}$ is preferably the same group as $R^{2b}$.

$Y^a$ and $Y^b$ are each independently an ester bond, an amide bond, a carbamate bond, an ether bond or a urea bond, preferably an ester bond, an amide bond or a carbamate bond, most preferably an ester bond. While the binding direction of $Y^a$ and $Y^b$ is not limited, when $Y^a$ is an ester bond, a structure of $R^{3a}$—CO—O—$R^{2a}$— is preferable, and when $Y^b$ is an ester bond, a structure of $R^{3b}$—CO—O—$R^{2b}$— is preferable.

$Y^a$ may be the same as or different from $Y^b$, and $Y^a$ is preferably the same group as $Y^b$.

$R^{3a}$ and $R^{3b}$ are each independently a sterol residue, a liposoluble vitamin residue or an aliphatic hydrocarbon group having 12-23 carbon atoms, preferably a liposoluble vitamin residue or an aliphatic hydrocarbon group having 12-23 carbon atoms.

As the "sterol residue", a residue derived from sterol or a sterol derivative, excluding a reactive functional group (e.g., hydroxyl group) involved in the binding with $Y^a$ or $Y^b$, can be mentioned, and preferred is a residue derived from a sterol derivative. The sterol derivative is, for example, a sterol hemiester obtained by reacting a hydroxyl group of sterol with one of the carboxylic acids of dicarboxylic acid (in this case, the other carboxylic acid becomes a reactive functional group). Examples of the sterol include cholesterol, cholestanol, stigmasterol, β-sitosterol, lanosterol, ergosterol and the like, with preference given to cholesterol and cholestanol. Examples of the dicarboxylic acid include malonic acid, succinic acid, glutaric acid, adipic acid and the like, with preference given to succinic acid and glutaric acid. Specific examples of the sterol derivative include cholesterol hemisuccinate, cholesterol hemiglutarate and the like.

As the "liposoluble vitamin residue", a residue derived from a liposoluble vitamin or a liposoluble vitamin derivative, excluding a reactive functional group (e.g., hydroxyl group) involved in the binding with $Y^a$ or $Y^b$, can be mentioned, and preferred is a residue derived from a liposoluble vitamin derivative. The liposoluble vitamin derivative is, for example, a liposoluble vitamin hemiester obtained by reacting a hydroxyl group of liposoluble vitamin whose reactive functional group is the hydroxyl group with one of the carboxylic acids of dicarboxylic acid (in this case, the other carboxylic acid becomes a reactive functional group). Examples of the liposoluble vitamin include retinoic acid, retinol, retinal, ergosterol, 7-dehydrocholesterol, calciferol, cholecalciferol, dihydroergocalciferol, dihydrotachysterol, tocopherol, tocotrienol and the like. The liposoluble vitamin is preferably retinoic acid or tocopherol, most preferably tocopherol. Examples of the dicarboxylic acid include malonic acid, succinic acid, glutaric acid, adipic acid and the like, with preference given to succinic acid and glutaric acid. Specific examples of the liposoluble vitamin derivative include tocopherol hemisuccinate, tocopherol hemiglutarate and the like.

The aliphatic hydrocarbon group having 12-23 carbon atoms may be linear or branched, preferably linear. The aliphatic hydrocarbon group may be saturated or unsaturated. In the case of an unsaturated hydrocarbon group, the aliphatic hydrocarbon group contains 1-6, preferably 1-3, most preferably 1-2 unsaturated bonds. While the unsaturated bond includes a carbon-carbon double bond and a carbon-carbon triple bond, it is preferably a double bond. The aliphatic hydrocarbon group has a carbon number of preferably 13-21, most preferably 13-17. While the aliphatic hydrocarbon group includes an alkyl group, an alkenyl group, an alkynyl group and the like, it is preferably an alkyl group or an alkenyl group. Examples of the aliphatic hydrocarbon group having 12-23 carbon atoms include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tricosyl group, tridecenyl group, tetradecenyl group, pentadecenyl group, hexadecenyl group, heptadecenyl group, octadecenyl group, nonadecenyl group, icosenyl group, henicosenyl group, docosenyl group, tricosenyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, methyldodecyl group, methyltridecyl group, methyltetradecyl group, methylpentadecyl group, methylheptadecyl group, methyloctadecyl group, methylnonadecyl group, methylicosyl group, methylhenicosyl group, methyldocosyl group, ethylundecyl group, ethyldodecyl group, ethyltridecyl group, ethyltetradecyl group, ethylpentadecyl group, ethylheptadecyl group, ethyloctadecyl group, ethylnonadecyl group, ethylicosyl group, ethylhenicosyl group, hexylheptyl group, hexylnonyl group, heptyloctyl group, heptyldecyl group, octylnonyl group, octylundecyl group, nonyldecyl group, decylundecyl group, undecyldodecyl group, hexamethylundecyl group and the like. As the linear one, preferred are dodecyl group, tridecyl group, pentadecyl group, heptadecyl group, nonadecyl group, henicosyl group, heptadecenyl group, heptadecadienyl group, particularly preferably, tridecyl group, heptadecyl group, heptadecenyl group, and heptadecadienyl group. As the branched one, preferred are methylpentadecyl group, hexylnonyl group, heptyldecyl group, octylundecyl group, and hexamethylundecyl group, and particularly preferred are methylpentadecyl group, hexylnonyl group, and heptyldecyl group.

In one embodiment, an aliphatic hydrocarbon group having 12-23 carbon atoms, which is derived from fatty acid, aliphatic alcohol, or aliphatic amine is used. When $R^{3a}$ (or $R^{3b}$) is derived from fatty acid, $Y^a$ (or $Y^b$) is an ester bond or an amide bond, and fatty acid-derived carbonyl carbon is included in $Y^a$ (or $Y^b$). For example, when linoleic acid is used, $R^{3a}$ (or $R^{3b}$) is a heptadecadienyl group.

$R^{3a}$ may be the same as or different from $R^{3b}$, and $R^{3a}$ is preferably the same group as $R^{3b}$.

In one embodiment, $X^a$ is the same as $X^b$, $n^a$ is the same as $n^b$, $R^{1a}$ is the same as $R^{1b}$, $R^{2a}$ is the same as $R^{2b}$, $R^{3a}$ is the same as $R^{3b}$, and $Y^a$ is the same as $Y^b$.

In one embodiment,
$X^a$ and $X^b$ are each independently $X^1$,
$R^4$ is an alkyl group having 1-3 carbon atoms, $n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond, and
$R^{3a}$ and $R^{3b}$ are each independently an aliphatic hydrocarbon group having 12-23 carbon atoms.

In one embodiment,
$X^a$ and $X^b$ are each $X^1$,
$R^4$ is an alkyl group having 1-3 carbon atoms, $n^a$ and $n^b$ are each 1,
$R^{1a}$ and $R^{1b}$ are each an alkylene group having 1-6 carbon atoms,
$R^{2a}$ and $R^{2b}$ are each an alkylene group having 1-6 carbon atoms,
$Y^a$ and $Y^b$ are each an ester bond,
$R^{3a}$ and $R^{3b}$ are each an aliphatic hydrocarbon group having 12-23 carbon atoms,
$X^a$ is the same as $X^b$,
$R^{1a}$ is the same as $R^{1b}$,
$R^{2a}$ is the same as $R^{2b}$, and
$R^{3a}$ is the same as $R^{3b}$.

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—, and
$R^{3a}$ and $R^{3b}$ are each independently an alkyl group or alkenyl group having 13-17 carbon atoms.

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—,
$R^{3a}$ and $R^{3b}$ are each an alkyl group or alkenyl group having 13-17 carbon atoms, and
$R^{3a}$ is the same as $R^{3b}$ In one embodiment,
$X^a$ and $X^b$ are each independently $X^1$,
$R^4$ is an alkyl group having 1-3 carbon atoms, $n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond, and
$R^{3a}$ and $R^{3b}$ are each independently a liposoluble vitamin residue (e.g., retinoic acid residue, tocopherol residue, group derived from tocopherol hemisuccinate).

In one embodiment,
$X^a$ and $X^b$ are each $X^1$,
$R^4$ is an alkyl group having 1-3 carbon atoms, $n^a$ and $n^b$ are each 1,
$R^{1a}$ and $R^{1b}$ are each an alkylene group having 1-6 carbon atoms,
$R^{2a}$ and $R^{2b}$ are each an alkylene group having 1-6 carbon atoms,
$Y^a$ and $Y^b$ are each an ester bond, $R^{3a}$ and $R^{3b}$ are each a liposoluble vitamin residue (e.g., retinoic acid residue, tocopherol residue, group derived from tocopherol hemisuccinate),
$X^a$ is the same as $X^b$,
$R^{1a}$ is the same as $R^{1b}$,
$R^{2a}$ is the same as $R^{2b}$, and
$R^{3a}$ is the same as $R^{3b}$.

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—, and
$R^{3a}$ and $R^{3b}$ are each independently a liposoluble vitamin residue (e.g., retinoic acid residue, tocopherol residue, group derived from tocopherol hemisuccinate).

In one embodiment,
$X^a$ and $X^b$ are each $X^1$,
$R^4$ is a methyl group, $n^a$ and $n^b$ are each 1,
$R^{1a}$ and $R^{1b}$ are each an ethylene group,
$R^{2a}$ and $R^{2b}$ are each a trimethylene group,
$Y^a$ and $Y^b$ are each —CO—O—,
$R^{3a}$ and $R^{3b}$ are each a liposoluble vitamin residue (e.g., retinoic acid residue, tocopherol residue, group derived from tocopherol hemisuccinate), and
$R^{3a}$ is the same as $R^{3b}$.

In one embodiment,
$X^a$ and $X^b$ are each independently $X^2$,
t is 2,
$n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond, and
$R^{3a}$ and $R^{3b}$ are each independently a liposoluble vitamin residue (e.g., retinoic acid residue, tocopherol residue, group derived from tocopherol hemisuccinate) or an aliphatic hydrocarbon group having 12-23 carbon atoms (e.g., alkyl group having 12-23 carbon atoms).

In one embodiment,
$X^a$ and $X^b$ are each independently $X^2$,
t is 2,
$n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond,
$R^{3a}$ and $R^{3b}$ are each independently a liposoluble vitamin residue (e.g., retinoic acid residue, tocopherol residue, group derived from tocopherol hemisuccinate) or an aliphatic hydrocarbon group having 12-23 carbon atoms (e.g., alkyl group having 12-23 carbon atoms),
$X^a$ is the same as $X^b$,
$R^{1a}$ is the same as $R^{1b}$,
$R^{2a}$ is the same as $R^{2b}$, and
$R^{3a}$ is the same as $R^{3b}$.

In one embodiment,
$X^a$ and $X^b$ are each independently $X^2$,
t is 2,
$n^a$ and $n^b$ are each 1,
$R^{1a}$ and $R^{1b}$ are each an ethylene group,
$R^{2a}$ and $R^{2b}$ are each independently an alkylene group having 1-6 carbon atoms,
$Y^a$ and $Y^b$ are each an ester bond,
$R^{3a}$ and $R^{3b}$ are each independently a liposoluble vitamin residue (e.g., retinoic acid residue, tocopherol residue, group derived from tocopherol hemisuccinate) or an aliphatic hydrocarbon group having 12-23 carbon atoms (e.g., alkyl group having 12-23 carbon atoms),
$X^a$ is the same as $X^b$,
$R^{2a}$ is the same as $R^{2b}$, and
$R^{3a}$ is the same as $R^{3b}$ In one embodiment,
$X^a$ and $X^b$ are 1,4-piperazinediyl groups,
$n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond, and
$R^{3a}$ and $R^{3b}$ are each independently a liposoluble vitamin residue (e.g., retinoic acid residue, tocopherol residue, group derived from tocopherol hemisuccinate) or an aliphatic hydrocarbon group having 12-23 carbon atoms (e.g., an alkyl group or alkenyl group having 12-23 (preferably 13-17) carbon atoms).

In one embodiment,
$X^a$ and $X^b$ are 1,4-piperazinediyl groups,
$n^a$ and $n^b$ are each 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each an ester bond,
$R^{3a}$ and $R^{3b}$ are each independently a liposoluble vitamin residue (e.g., retinoic acid residue, tocopherol residue, group derived from tocopherol hemisuccinate) or an aliphatic hydrocarbon group having 12-23 carbon atoms (e.g., an alkyl group or alkenyl group having 12-23 (preferably 13-17) carbon atoms),
$R^{2a}$ is the same as $R^{2b}$, and
$R^{3a}$ is the same as $R^{3b}$ In one embodiment,
$X^a$ and $X^b$ are 1,4-piperazinediyl groups,
$n^a$ and $n^b$ are each 1,
$R^{1a}$ and $R^{1b}$ are ethylene groups,
$R^{2a}$ and $R^{2b}$ are ethylene groups,
$Y^a$ and $Y^b$ are each —CO—O—, and
$R^{3a}$ and $R^{3b}$ are each independently a liposoluble vitamin residue (e.g., retinoic acid residue, tocopherol residue, group derived from tocopherol hemisuccinate) or an aliphatic hydrocarbon group having 12-23 carbon atoms (e.g., an alkyl group or alkenyl group having 12-23 (preferably 13-17) carbon atoms).

In one embodiment,
$X^a$ and $X^b$ are 1,4-piperazinediyl groups,
$n^a$ and $n^b$ are each 1,
$R^{1a}$ and $R^{1b}$ are ethylene groups,
$R^{2a}$ and $R^{2b}$ are ethylene groups,
$Y^a$ and $Y^b$ are each —CO—O—, and
$R^{3a}$ and $R^{3b}$ are each independently a liposoluble vitamin residue (e.g., retinoic acid residue, tocopherol residue, group derived from tocopherol hemisuccinate) or of an aliphatic hydrocarbon group having 12-23 carbon atoms (e.g., an alkyl group or alkenyl group having 12-23 (preferably 13-17) carbon atoms), and
$R^{3a}$ is the same as $R^{3b}$.

Specific examples of the compound of the formula (1) include the compounds of the following B-2, B-2-2, B-2-3, B-2-4, B-2-5, TS-C4E, TS-C5P, TS-P2C1, TS-P3C1, TS-P4C1, TS-P4C2, TS-P4C3, TS-P4C4, TG-C3M, TSamide-C3M, TS-PZ4C2, O-C3M, L-PZ4C2.

TABLE 1
| compound name | structure |
|---|---|
| B-2 | 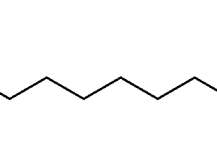 |
| B-2-2 | 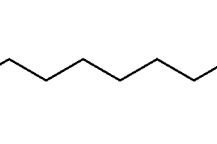 |
| B-2-3 | 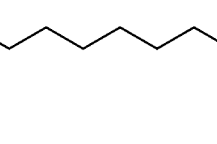 |
| B-2-4 | 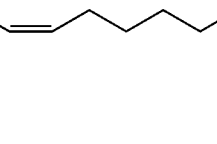 |
| B-2-5 | 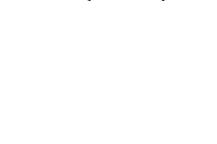 |

TABLE 1-continued
| compound name | structure |
|---|---|
| TS-C4E | 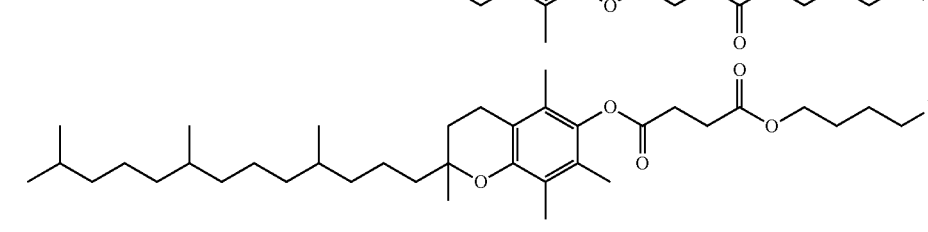 |
| TS-C5P | 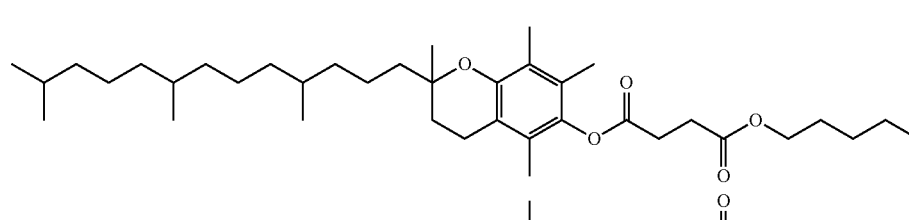 |
| TS-P2C1 | 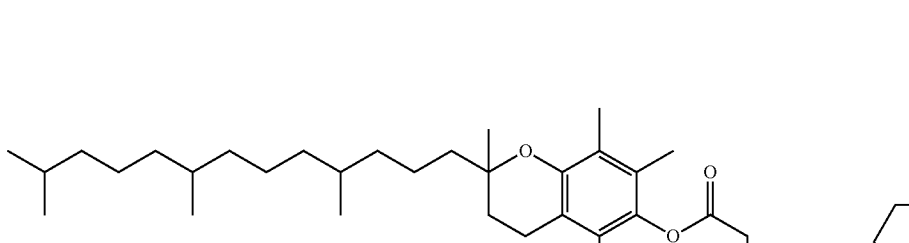 |

TABLE 1-continued
| compound name | structure |
| --- | --- |
| TS-P3C1 | 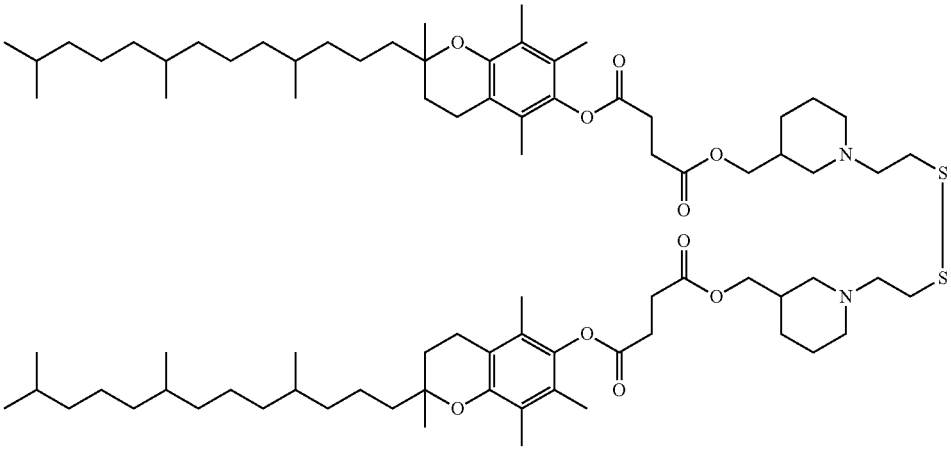 [SMILES: Cc1c(C)c2c(c(C)c1OC(=O)CCC(=O)OCC1CCCN(CCSSCCN3CCCC(COC(=O)CCC(=O)Oc4c(C)c(C)c5c(c4C)CCC(C)(CCCC(C)CCCC(C)CCCC(C)C)O5)C3)C1)CCC(C)(CCCC(C)CCCC(C)CCCC(C)C)O2] |
| TS-P4C1 | 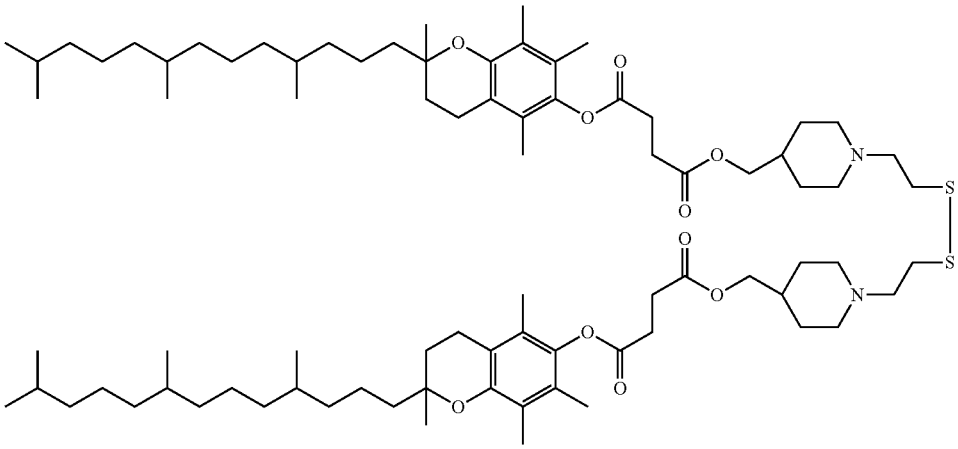 [SMILES: Cc1c(C)c2c(c(C)c1OC(=O)CCC(=O)OCC1CCN(CCSSCCN3CCC(COC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| TS-P4C2 | 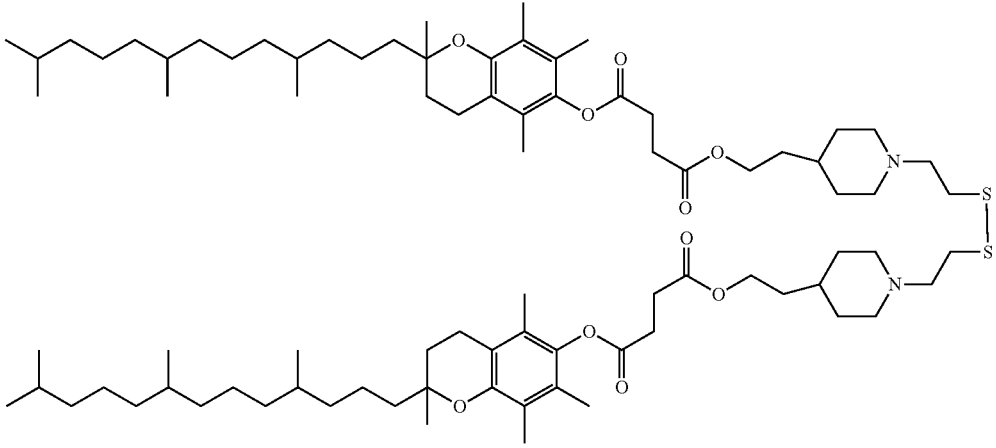 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |

TABLE 1-continued

| compound name | structure |
| --- | --- |
| TS-P4C3 | 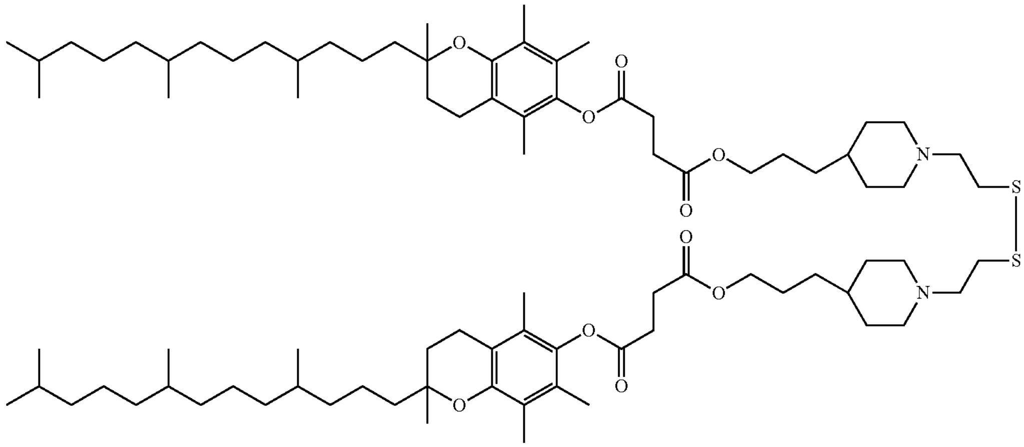 [SMILES: Cc1c(C)c2c(c(C)c1OC(=O)CCC(=O)OCCCC1CCN(CCSSCCN3CCC(CCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| TS-P4C4 | 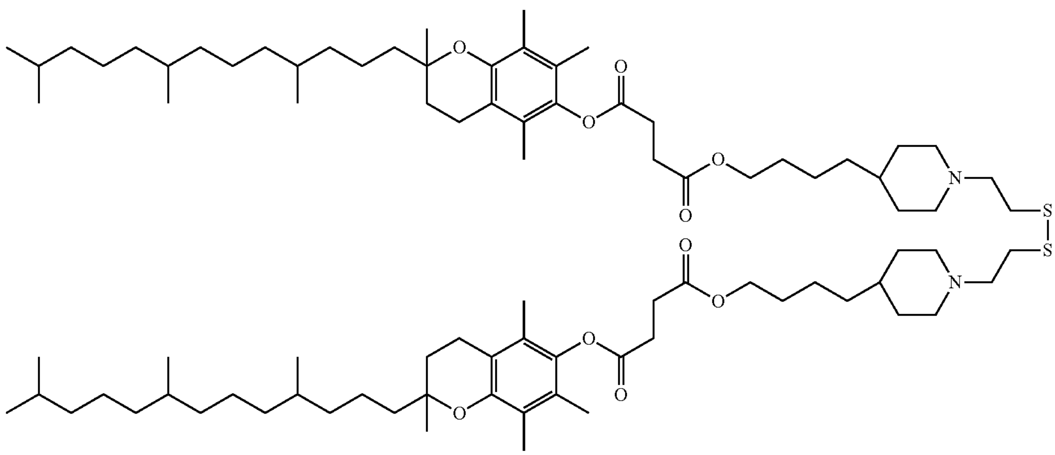 [SMILES: Cc1c(C)c2c(c(C)c1OC(=O)CCC(=O)OCCCCC1CCN(CCSSCCN3CCC(CCCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| TG-C3M | 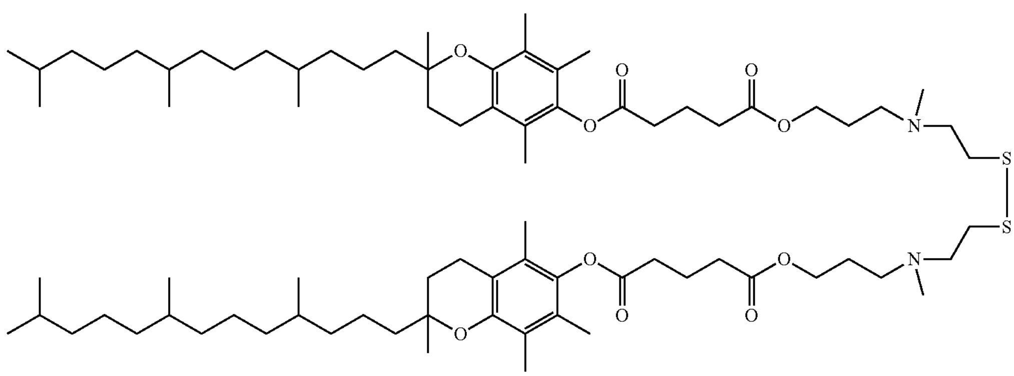 [SMILES: Cc1c(C)c2c(c(C)c1OC(=O)CCCC(=O)OCCCN(C)CCSSCCN(C)CCCOC(=O)CCCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| TSamide-C3M | 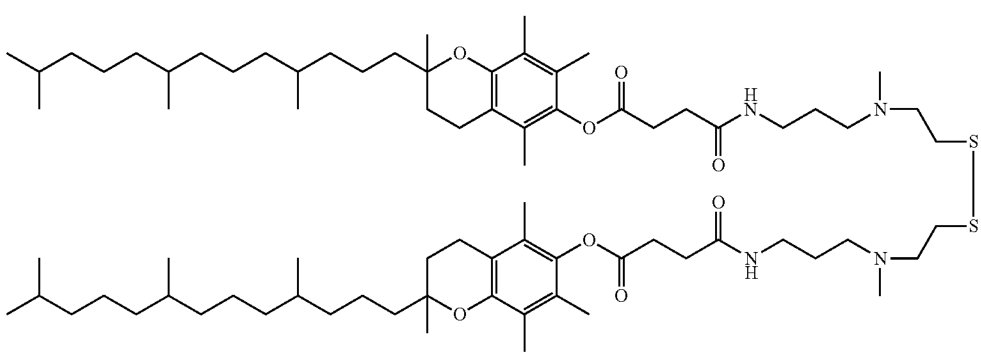 [SMILES: Cc1c(C)c2c(c(C)c1OC(=O)CCC(=O)NCCCN(C)CCSSCCN(C)CCCNC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

TABLE 1-continued

| compound name | structure |
|---|---|
| TS-PZ4C2 | 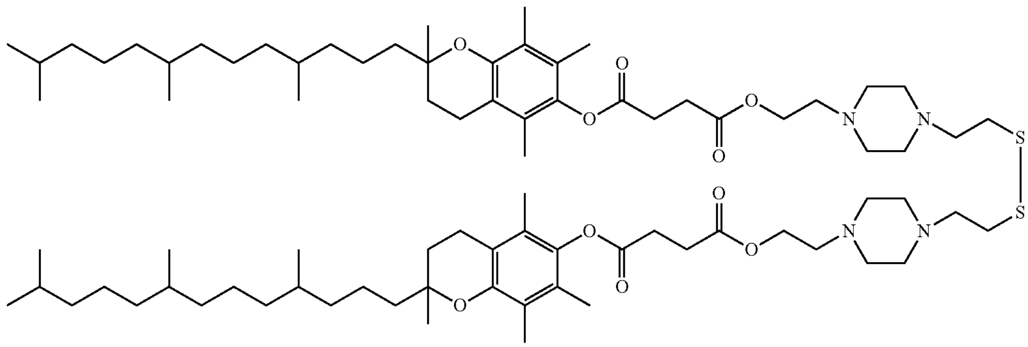 [SMILES: Cc1c(C)c2c(c(C)c1OC(=O)CCC(=O)OCCN1CCN(CCSSCCN3CCN(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| O-C3M | 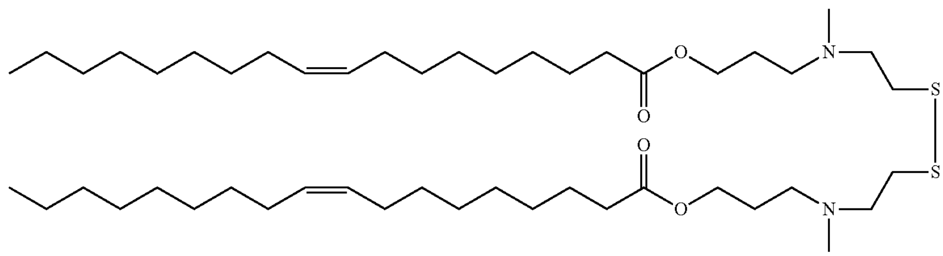 [SMILES: CCCCCCCC/C=C\CCCCCCCC(=O)OCCCN(C)CCSSCCN(C)CCCOC(=O)CCCCCCC/C=C\CCCCCCCC] |
| L-PZ4C2 | 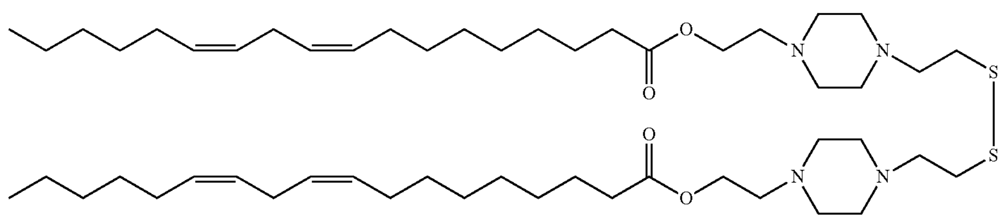 [SMILES: CCCCC/C=C\C/C=C\CCCCCCCC(=O)OCCN1CCN(CCSSCCN2CCN(CCOC(=O)CCCCCCC/C=C\C/C=C\CCCCC)CC2)CC1] |

Of the compounds represented by the formula (1), a compound wherein $X^a$ and $X^b$ are respectively $X^1$ and $X^2$ can be produced by the method described in WO 2013/073480 A1 or US 2014/0335157 A1.

The production method of a compound represented by the formula (1) wherein $X^a$ and $X^b$ are 1,4-piperazinediyl groups is explained.

The compound of the formula (1) has an —S—S— (disulfide) bond. Therefore, the production method includes, for example, a method including producing SH (thiol) compound having $R^{3a}$—$(Y^aR^{2a})n^a$—$X^a$—$R^{1a}$— and SH (thiol) compound having $R^{3b}$—$(Y^b$—$R^{2b})n^b$—$X^b$—$R^{1b}$—, subjecting them to oxidation (coupling) to give the compound of the present invention containing —S—S— bond, a method including sequentially bonding necessary parts to a compound containing an —S—S— bond to finally obtain the compound of the present invention and the like. Preferred is the latter method.

A specific example of the latter method is shown below; however, the production method is not limited thereto.

Examples of the starting compound include both-terminal carboxylic acid, both-terminal amine, both-terminal isocyanate, both-terminal alcohol, both-terminal alcohol having a leaving group such as methanesulfonyl group and the like, both-terminal carbonate having a leaving group such as p-nitrophenylcarbonate group and the like, and the like, each of which has an —S—S— bond.

For example, when a compound wherein $X^a$ and $X^b$ are 1,4-piperazinediyl groups, $R^{1a}$ and $R^{1b}$ are ethylene groups, $n^a$ and $n^b$ are each 1, $R^{2a}$ and $R^{2b}$ are ethylene groups, $Y^a$ and $Y^b$ are the same and Y (ester bond, amide bond, carbamate bond, or ether bond), and $R^{3a}$ and $R^{3b}$ are the same and $R^3$ (sterol residue, liposoluble vitamin residue, or aliphatic hydrocarbon group having 13-23 carbon atoms) is produced, both-terminal functional groups of compound (I) containing an —S—S— bond are reacted with a secondary amino group at the 1-position of a piperazine derivative having a functional group at the 4-position via an ethylene group (hereinafter to be referred to as "compound (II)"), and the functional group in the derivative (II) is reacted with a functional group in compound (III) containing $R^3$—Y, whereby the compound of the formula (1) containing an —S—S— bond, $R^{1a}$ and $R^{1b}$, two piperazine skeletons, $R^{2a}$ and $R^{2b}$, $Y^a$ and $Y^b$, and $R^{3a}$ and $R^{3b}$ can be obtained.

In the reaction of compound (I) and compound (II), a base catalyst such as potassium carbonate, sodium carbonate, potassium hydroxide or the like may be used as a catalyst, or the reaction may be performed without a catalyst. Preferably, potassium carbonate or sodium carbonate is used as a catalyst.

The amount of the catalyst is 0.1-100 molar equivalents, preferably, 0.1-20 molar equivalents, more preferably 0.1-5 molar equivalents, relative to compound (I). The amount of compound (II) to be charged is 1-50 molar equivalents, preferably 1-10 molar equivalents, relative to compound (I).

The solvent to be used for the reaction of compound (I) and compound (II) is not particularly limited as long as it is a solvent or aqueous solution that does not inhibit the reaction. For example, ethyl acetate, dichloromethane, chloroform, acetonitrile, toluene and the like can be mentioned. Among these, toluene, chloroform and acetonitrile are preferable.

The reaction temperature is −20 to 150° C., preferably 0 to 80° C., more preferably 20 to 50° C., and the reaction time is 1-48 hr, preferably 2-24 hr.

When the reaction product (hereinafter to be referred to as reaction product (I)) of compound (I) and compound (II) is reacted with compound (III), an alkali catalyst such as potassium carbonate, sodium carbonate, potassium hydroxide or the like, like the catalyst used for the reaction of compound (I) and compound (II), or an acid catalyst such as p-toluenesulfonic acid, methanesulfonic acid or the like may be used, or the reaction may be performed without a catalyst.

In addition, the reaction product (I) may be directly reacted with compound (III) by using a condensing agent such as dicyclohexylcarbodiimide (hereinafter to be referred to as "DCC"), diisopropylcarbodiimide (hereinafter to be referred to as "DIC"), 1-ethyl-3-(3-dimethylaminopropyl)carbodiimide hydrochloride (hereinafter to be referred to as "EDC") or the like. Alternatively, compound (III) may be treated with a condensing agent to be converted to an anhydride and the like, after which it is reacted with the reaction product (I).

The amount of compound (III) to be charged is 1-50 molar equivalents, preferably 1-10 molar equivalents, relative to the reaction product (I).

The catalyst to be used for the reaction of reaction product (I) and compound (III) is appropriately selected according to the functional groups to be reacted.

The amount of catalyst is 0.05-100 molar equivalents, preferably 0.1-20 molar equivalents, more preferably 0.2-5 molar equivalent, relative to reaction product (I).

The solvent to be used for the reaction of reaction product (I) and compound (III) is not particularly limited as long as it is a solvent or aqueous solution that does not inhibit the reaction. For example, ethyl acetate, dichloromethane, chloroform, acetonitrile, toluene and the like can be mentioned. Among these, chloroform and toluene are preferable.

The reaction temperature is 0 to 150° C., preferably 0 to 80° C., more preferably 20 to 50° C., and the reaction time is 1 hr-48 hr, preferably 2-24 hr.

The reaction product obtained by the above-mentioned reaction can be appropriately purified by a general purification method such as extraction purification, recrystallization, adsorption purification, reprecipitation, column chromatography, ion exchange chromatography or the like.

Those of ordinary skill in the art can produce a desired compound of the formula (1) by appropriately selecting the starting material and performing the reactions according to the method of the Examples in the present specification.

The O/W type emulsion of the present invention is explained below.

The O/W type emulsion refers to an emulsion in which oil droplets are dispersed in an aqueous phase. The oil droplets may or may not contain an unshaped layered structure (layered lipid bilayer membrane). When oil droplets contain a layered lipid bilayer membrane, an aqueous phase may be present between a lipid bilayer membrane and a lipid bilayer membrane. The O/W type emulsion of the present invention contains a compound of the formula (1) in the oil droplets constituting the emulsion.

The O/W type emulsion of the present invention may contain, in addition to the compound of the formula (1), other lipids (e.g., phospholipid, sterol, PEG lipid, glycolipid, peptide lipid, cationic lipid other than the compound of the formula (1)) in the oil droplets. The O/W type emulsion of the present invention preferably contains at least one lipid selected from the group consisting of PEG lipid, phospholipid and sterol, more preferably PEG lipid, in the oil droplets in addition to the compound of the formula (1). In one embodiment, the O/W type emulsion of the present invention contains PEG lipid in the oil droplets, in addition to the compound of the formula (1), and at least one lipid selected from the group consisting of phospholipid and sterol. In a preferable embodiment, the O/W type emulsion of the present invention contains, in the oil droplets, phospholipid, PEG lipid and sterol in addition to the compound of the formula (1).

PEG lipid means a lipid containing modification by PEG. When PEG lipid is contained in the oil droplets of the O/W type emulsion of the present invention, it forms a PEG hydration layer on the interface, prevents coagulation between particles and between particles and protein, and maintains the volume median diameter stable at 100 nm or below during preparation and after preparation. Examples of the PEG lipid to be used for the O/W type emulsion of the present invention include PEG phospholipid in which polyethylene glycol is bonded to the above-mentioned phospholipid, and diacyl glycerol PEG in which polyethylene glycol is bonded to diacyl glycerol to which the above-mentioned acyl group having 8-24 carbon atoms is bonded. The molecular weight of the polyethylene glycol constituting the PEG lipid is not particularly limited. It is preferably 200-10000, more preferably 2000-5000. PEG lipid to be used for the O/W type emulsion of the present invention is preferably diacyl glycerol PEG in which the acyl group is saturated, more preferably diacyl glycerol PEG in which the acyl group is a myristoyl group or a stearoyl group, further preferably diacyl glycerol PEG in which a myristoyl group and polyethylene glycol having a molecular weight of 2000 are bonded (DMG-PEG2000) or diacyl glycerol PEG in which a stearoyl group and polyethylene glycol having a molecular weight of 2000 are bonded (DSG-PEG2000).

When phospholipid is contained in the oil droplets of the O/W type emulsion of the present invention, it stabilizes the water/oil interface thereof, affords stability in the presence of protein such as in blood or medium, and stably lowers the volume median diameter to not more than 100 nm, which is suitable for administration to the body. Examples of the phospholipid include natural or synthetic phospholipids such as phosphatidylcholine (PC), phosphatidylethanolamine (PE), phosphatidylserine (PS), phosphatidylinositol (PI), phosphatidylglycerol (PG), phosphatidic acid (PA), dicetyl phosphoric acid, sphingomyelin (SPM), cardiolipin and the like; partially or fully hydrogenated products of these phospholipids; natural lecithins such as soybean lecithin, corn lecithin, cottonseed oil lecithin, egg-yolk lecithin and the like, which are mixtures of these phospholipids; and hydrogenated soybean lecithin, hydrogenated egg-yolk lecithin and the like. The hydrocarbon group constituting these phospholipids has the 1-position and the 2-position which may be the same or different, and is constituted by an acyl group having 8-24 carbon atoms. Examples of the acyl group having 8-24 carbon atoms include the residues obtained by excluding hydroxyl group from fatty acids such as caprylic acid, pelargric acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, myristoleic acid, palmitoleic acid, oleic acid, eicosenoic acid, erucic acid, hexadecadienoic acid, linoleic acid, eicosadienoic acid, docosadienoic acid, hexadecatrienoic acid, α-linolenic acid, γ-linolenic acid, eicosatrienoic acid, arachidonic acid, eicosapentaenoic acid, docosatetraenoic acid, docosahexaenoic acid and the like.

The phospholipid to be used for the O/W type emulsion of the present invention is preferably synthetic phospholipid, more preferably synthetic phospholipid containing an unsaturated bond in the acyl group, further preferably dioleoylphosphatidylcholine (DOPC) or dioleoylphosphatidylethanolamine (DOPE), further preferably dioleoylphosphatidylcholine (DOPC).

When sterol is contained in the oil droplets of the O/W type emulsion of the present invention, it structurally stabilizes emulsion as a molecular assembly, and stably lowers the particle size (volume median diameter) to not more than 100 nm, which is suitable for administration to the body. Examples of the sterol used in the O/W type emulsion of the present invention include cholesterol, phytosterol, dihydrocholesterol, cholestryl stearate, cholesteryl nonanoate, cholestryl hydroxystearate, dihydrocholesteryl oleate and the like, preferably cholesterol, phytosterol, cholestryl stearate, further preferably cholesterol.

The content of the lipid contained in the O/W type emulsion of the present invention is not particularly limited as long as the hardly water-soluble drug can be introduced and released in the cells. Generally, the total lipid (excluding PEG lipid) concentration of the emulsion is 0.5 mM-10 mM, preferably, 1 mM-8 mM.

The content of the compound of the formula (1) contained in the O/W type emulsion of the present invention is not particularly limited. Generally, when the O/W type emulsion is used as a carrier for delivering the below-mentioned hardly water-soluble drug into cells, the compound of the formula (1) in an amount sufficient for introducing and releasing a hardly water-soluble drug in cells is contained in the O/W type emulsion of the present invention. For example, it is 5-100 mol %, preferably 10-70 mol %, more preferably 30-50 mol %, of the total lipid (excluding PEG lipid) constituting the oil droplets.

When the O/W type emulsion of the present invention contains PEG lipid, the content thereof is not particularly limited as long as the O/W type emulsion of the present invention can introduce and release a hardly water-soluble drug in cells. When the total of the contents of the lipids other than PEG lipid constituting the oil droplets contained in the O/W type emulsion of the present invention is 100 molar equivalents, for example, not less than 1 molar equivalent, preferably not less than 3 molar equivalents, more preferably not less than 5 molar equivalents, of PEG lipid is additionally contained in the O/W type emulsion of the present invention. The upper limit of the content of the PEG lipid is not particularly limited as long as introduction and release of a hardly water-soluble drug in cells by the O/W type emulsion of the present invention is not prevented. When the total of the contents of the lipids other than PEG lipid constituting the oil droplets contained in the O/W type emulsion of the present invention is 100 molar equivalents, the content of the PEG lipid in the O/W type emulsion of the present invention is, for example, not more than 20 molar equivalents, preferably not more than 18 molar equivalents, more preferably not more than 15 molar equivalents. In a further aspect, when the total of the contents of the lipids other than PEG lipid constituting the oil droplets contained in the O/W type emulsion of the present invention is 100 molar equivalents, the content of the PEG lipid in the O/W type emulsion of the present invention is, for example, not more than 30 molar equivalents, preferably not more than 25 molar equivalents, more preferably not more than 20 molar equivalents. Therefore, when the total of the contents of the lipids other than PEG lipid constituting the oil droplets contained in the O/W type emulsion of the present invention is 100 molar equivalents, for example, 1-20 molar equivalents, preferably 3-18 molar equivalents, more preferably 5-15 molar equivalents of PEG lipid is additionally contained in the O/W type emulsion of the present invention. In a further aspect, when the total of the contents of the lipids other than PEG lipid constituting the oil droplets contained in the O/W type emulsion of the present invention is 100 molar equivalents, for example, 1-30 molar equivalents, preferably 3-25 molar equivalents, more preferably 5-20 molar equivalents, of PEG lipid is additionally contained in the O/W type emulsion of the present invention.

When the O/W type emulsion of the present invention contains phospholipid, the content thereof is not particularly limited as long as introduction and release of a hardly water-soluble drug in cells by the O/W type emulsion of the present invention is not prevented. For example, it is 10-70 mol %, preferably 20-60 mol %, more preferably 30-50 mol %, of the total lipid (excluding PEG lipid) constituting the oil droplets contained in the O/W type emulsion of the present invention.

When the O/W type emulsion of the present invention contains sterol, the content thereof is not particularly limited as long as introduction and release of a hardly water-soluble drug in cells by the O/W type emulsion of the present invention is not prevented. For example, it is 10-50 mol %, preferably 20-40 mol %, of the total lipid (excluding PEG lipid) constituting the oil droplets contained in the O/W type emulsion of the present invention.

The O/W type emulsion of the present invention may further contain, in the oil droplets constituting same, components other than lipid, for example, surfactant (e.g., CHAPS, sodium cholate, octylglucoside, N-D-gluco-N-methylalkaneamides etc.), polyethylene glycol, protein, hardly water-soluble drug (below-mentioned) and the like.

The O/W type emulsion of the present invention may contain, in the aqueous phase constituting same, appropriate buffering agent (e.g., phosphoric acid or a salt thereof, malic acid or a salt thereof, carbonic acid or a salt thereof), salt (e.g., NaCl, KCl), hydrophilic solvent other than water (e.g., acetone, ether solvents such as 1,2-dimethoxyethane, 1,4-dioxane, tetrahydrofuran and the like, alcohol solvents such as methanol, ethanol, propanol, isopropanol, butanol, isobutanol, tert-butanol and the like; preferably alcohol solvents; more preferably ethanol or tert-butanol) and the like, in addition to water.

The volume median diameter of the O/W type emulsion of the present invention (volume median diameter of oil droplets constituting the O/W type emulsion of the present invention) is not more than 100 nm, preferably not more than 70 nm, more preferably not more than 50 nm. When the volume median diameter is set to not more than 100 nm and the emulsion is administered to the body, discharge from the spleen can be avoided, retentivity in blood becomes high and efficient delivery to a deep part of tissues such as tumor and the like becomes possible. The lower limit of the volume median diameter of the O/W type emulsion of the present invention is not particularly limited. However, from the aspects of production techniques, it is generally not less than 20 nm, preferably not less than 25 nm, more preferably not less than 30 nm. The volume median diameter of the O/W type emulsion of the present invention is generally 20-100 nm, preferably 25-70 nm, more preferably 30-50 nm.

The O/W type emulsion of the present invention can be prepared by dissolving the compound of the formula (1) and other constituent components (lipid etc.) in a suitable solvent, mixing the obtained lipid solution with an aqueous buffer solution, and dispersing the obtained lipid solution in a water system. A method for mixing the lipid solution and the aqueous buffer solution is not particularly limited, and a method capable of rapidly affording a uniform emulsion is preferable. A method for mixing the lipid solution and the aqueous buffer solution is exemplified by a method including continuous mixing using a microchannel and the like and a method including discontinuous mixing by vigorous stirring using a vortex mixer and the like. When mixing is performed by a discontinuous method using a vortex mixer and the like, the total amount of one of the lipid solution and the aqueous buffer solution is added while stirring the other. The mixing time until homogeneous emulsification is achieved is preferably as short as possible, and it is, for example, within 10 seconds, preferably within 5 seconds, more preferably within 3 seconds.

As a solvent used for preparing the lipid solution, any solvent may be used as long as it dissolves the lipid and is miscible with water. Examples of such solvent include ether solvents such as 1,2-dimethoxyethane, 1,4-dioxane, tetrahydrofuran and the like; alcohol solvents such as methanol, ethanol, propanol, isopropanol, butanol, isobutanol, tert-butanol and the like, preferably alcohol solvents, more preferably ethanol or tert-butanol, and the like. While the lipid concentration of a lipid solution is not particularly limited as long as the O/W type emulsion of the present invention can be prepared, the total concentration of the total lipid (excluding PEG lipid) is adjusted to, for example, 1-12.5 mM, preferably 2-3 mM.

The pH of the aqueous buffer solution is not particularly limited as long as the O/W type emulsion of the present invention can be prepared. To stably control volume median diameter of the O/W type emulsion to 100 nm or below, it is preferable to adjust the aqueous buffer solution from weakly acidic to neutral, preferably weakly acidic. The pH of the aqueous buffer solution is, for example, 3.0-7.4, preferably 3.0-5.0.

While the kind of the aqueous buffer solution is not particularly limited as long as it does not show reducibility, one having a buffer action in the aforementioned pH range is preferable. Examples thereof include aqueous buffer solutions of carbonic acid, HEPES, MES, succinic acid, malic acid, tartaric acid, lactic acid, phthalic acid, acetic acid, phosphoric acid, aspartic acid, glutamic acid, glycine and the like. The aqueous buffer solution is preferably an aqueous malic acid buffer solution. These aqueous buffer solutions can be adjusted to an appropriate pH by using alkali such as NaOH, KOH or the like.

The concentration of the buffering agent in the aqueous buffer solution is not particularly limited as long as the solution has an appropriate buffer action and is not precipitated in a lipid solution/aqueous buffer solution. In the case of, for example, an aqueous malic acid buffer solution, it is generally 1-100 mM, preferably 10-30 mM.

An inorganic salt may be dissolved in an aqueous buffer solution. The inorganic salt is not particularly limited. Examples thereof include halides (chloride etc.) and sulfates of alkali metals (Li, Na, K etc.) or alkaline earth metals (Ca etc.). The inorganic salt is preferably NaCl or KCl, more preferably NaCl. When the salt concentration is high, the volume median diameter of the O/W type emulsion tends to be higher. Thus, to stably control the volume median diameter of the O/W type emulsion to 100 nm or below, the salt concentration is preferably 0-0.5 M, more preferably 0-0.08 M, as the total halogen ion concentration.

The mixing volume ratio of the aqueous buffer solution and the lipid solution is not particularly limited as long as the O/W type emulsion of the present invention can be prepared. Generally 25-400 parts by volume, preferably 42-233 parts by volume, more preferably 66-150 parts by volume, further preferably 100 parts by volume, of the aqueous buffer solution is mixed per 100 parts by volume of the lipid solution. The total volume of the lipid solution and the aqueous buffer solution is not limited.

In a preferable embodiment, an alcohol solution of a lipid containing the compound of the formula (1) and an aqueous buffer solution having pH 3.0-7.4 and a salt concentration of 0-0.5 M are mixed and emulsified to give the O/W type emulsion of the present invention.

The aqueous phase of the O/W type emulsion obtained by emulsification may contain a considerable amount of the solvent of the lipid solution. After emulsification is completed, therefore, the aqueous phase of the O/W type emulsion may be replaced with a biocompatible buffered aqueous solution by subjecting the emulsified product to dialysis or ultrafiltration. The biocompatible buffer is not limited as long as it does not show toxicity to the body and, for example, PBS or the like is used. In this case, a biocompatible buffer may be added to the emulsified product prior to dialysis or ultrafiltration. For example, a biocompatible buffer in a volume about 3.2- to 4.0-fold that of the emulsified product is added, and dialysis or an ultrafiltration treatment is performed. The buffer replacement treatment is preferably performed continuously from the emulsion treatment, and dialysis or an ultrafiltration treatment is started, for example, within 30 min, preferably within 10 min, more preferably within 1 min, after completion of emulsification. To remove solvent contained in the lipid solution as much as possible, the replacement operation may be performed two or more times. The upper limit of the number of replacement is not limited.

The O/W type emulsion of the present invention can stably contain any hardly water-soluble drug encapsulated in the oil droplets constituting the emulsion. The O/W type emulsion encapsulating a hardly water-soluble drug of the present invention is easily taken up in a cell and the hardly water-soluble drug is efficiently introduced into the cell. Generally, when a hardly water-soluble drug is introduced into a cell by using a carrier, even if the hardly water-soluble drug is successfully introduced into the cell, the drug cannot exert its efficacy sufficiently when the hardly water-soluble drug is incorporated in the carrier in the cell. However, in the case of the O/W type emulsion of the present invention, since a compound represented by the formula (1) is rapidly decomposed due to the reductive environment in the cell, the O/W type emulsion is disintegrated and the encapsulated hardly water-soluble drug is rapidly released in the cell and can exhibit its efficacy. Therefore, the O/W type emulsion of the present invention is useful as a carrier for delivering a hardly water-soluble drug into a cell.

A hardly water-soluble drug can be encapsulated in the O/W type emulsion of the present invention by emulsification using a lipid solution containing the hardly water-soluble drug dissolved therein in the aforementioned preparation of the O/W type emulsion. The present invention also provides the above-mentioned O/W type emulsion of the present invention encapsulating a hardly water-soluble drug.

The hardly water-soluble drug in the present invention means a drug having a water/octanol distribution coefficient Log Pow, which is used for evaluating the hydrophobicity of a compound, of not less than 4. Examples of such hardly water-soluble drug include tacrolimus (Log Pow: 4.79), ursodeoxycholic acid (Log Pow: 4.76), oxethazaine (Log Pow: 4.38), simvastatin (Log Pow: 4.72), ethinylestradiol (Log Pow: 4.11), clotrimazole (Log Pow: 4.93), zaltoprofen (Log Pow: 4.25), betamethasone valerate (Log Pow: 4.14), pentazocine (Log Pow: 4.15), iotroxatic acid (Log Pow: 4.32), indomethacin (Log Pow: 4.25), ketoconazole (Log Pow: 4.04), danazol (4.94), bifonazole (Log Pow: 4.69), beclopetasone propionate (Log Pow: 4.07), mestranol (Log Pow: 4.94), acemetacin (Log Pow: 4.49), ipriflavone (Log Pow: 4.25), carvedilol (Log Pow: 4.07), domperidone (Log Pow: 4.05), mefenamic acid (Log Pow: 4.83), itraconazole (Log Pow: 5.00), reserpine (Log Pow: 4.45), chlorhexidine (Log Pow: 4.58), clinofibrate (Log Pow: 6.33), riboflavin butyrate (Log Pow: 6.25), siccanin (Log Pow: 6.10), mequitazine (Log Pow: 5.20), ebastine (Log Pow: 6.81), benidipine (Log Pow: 5.56), benzbromarone (Log Pow: 6.65), estradiol benzoate (Log Pow: 5.10), pimozide (Log Pow: 5.76), midecamycin acetate (Log Pow: 5.58), tolnaftate (Log Pow: 5.14), mepitiostane (Log Pow: 6.89), dexamethasone palmitate (Log Pow: 8.13), 4-methylumbelliferone palmitate (Log Pow: 7.92), ergocalciferol (Log Pow: 9.15), cholecalciferol (Log Pow: 9.08), tocopherol (Log Pow: 10.96), tocopheryl acetate (Log Pow: 10.69), tocopherol nicotinate (Log Pow: 11.33), phytonadione (Log Pow: 10.31), fluphenazine enanthate (Log Pow: 7.29), menatetrenone (Log Pow: 8.79), retinol acetate (Log Pow: 7.19), chloramphenicol palmitate (Log Pow: 8.69), candesartancilexetil (7.21), retinol palmitate (Log Pow: 14.32), ubidecarenone (Log Pow: 19.12), dexamethasone cholesterol hemisuccinate (Log Pow: 9.37), 4-methylumbelliferone cholesterol hemisuccinate (Log Pow: 9.16) and the like.

In a further aspect, the present invention also provides even dexamethasone cholesterol hemisuccinate and 4-methylumbelliferone cholesterol hemisuccinate. The compounds are useful as antitumor agents and the like. In the present invention, when the compounds are used as hardly water-soluble drugs, retentivity in blood becomes high due to the effect of cholesterol hemisuccinate and high efficacy can be expected as compared to unesterified dexamethasone and 4-methylumbelliferone. In the following, specific examples of the synthesis of dexamethasone cholesterol hemisuccinate and 4-methylumbelliferone cholesterol hemisuccinate are recited, to which the production method is not limited thereto.

A desired compound can be synthesized by reacting hydroxyl group of dexamethasone or 4-methylumbelliferone with carboxylic acid of cholesterol hemisuccinate. For this reaction, an alkali catalyst such as potassium carbonate, sodium carbonate, potassium hydroxide or the like, or an acid catalyst such as p-toluenesulfonic acid, methanesulfonic acid or the like may be used, or the reaction may be performed without a catalyst.

In addition, a condensing agent such as dicyclohexylcarbodiimide (hereinafter to be referred to as "DCC"), diisopropylcarbodiimide (hereinafter to be referred to as "DIC"), 1-ethyl-3-(3-dimethylaminopropyl)carbodiimide hydrochloride (hereinafter to be referred to as "EDC"), N,N-dimethyl-4-aminopyridine (hereinafter sometimes to be referred to as "DMAP"), N,N-diisopropylethylamine (hereinafter sometimes to be referred to as "DIPEA") or the like may be used. It is also possible to convert cholesterol hemisuccinate to anhydride and the like by using a condensing agent, and react same with hydroxyl group of dexamethasone or 4-methylumbelliferone.

The amount of cholesterol hemisuccinate to be added is 1-50 molar equivalents, preferably 1-10 molar equivalents, relative to a drug having a hydroxyl group.

The amount of the catalyst is 0.05-100 molar equivalents, preferably, 0.1-20 molar equivalents, more preferably 0.2-5 molar equivalents, relative to the reaction product.

The solvent to be used for the reaction is not particularly limited as long as it is a solvent that does not inhibit the reaction. Examples thereof include ethyl acetate, dichloromethane, chloroform, acetonitrile, toluene, dimethylformamide and the like. Among these, chloroform, toluene and dimethylformamide are preferable.

The reaction temperature is 0-150° C., preferably 0 to 80° C., more preferably 20 to 50° C., and the reaction time is 1-48 hr, preferably 2-24 hr.

The reaction product obtained by the above-mentioned reaction can be appropriately purified by a general purification method such as extraction purification, recrystallization, adsorption purification, reprecipitation, column chromatography, ion exchange chromatography or the like.

Those of ordinary skill in the art can produce a desired compound by appropriately selecting the starting material and performing the reactions according to the method of the Reference Examples of the present specification.

When a hardly water-soluble drug has higher hydrophobicity, it is expected to be more easily encapsulated in the O/W type emulsion of the present invention. Thus, the Log Pow of a hardly water-soluble drug to be used in the present invention is preferably higher, preferably not less than 5, more preferably not less than 7, further preferably not less than 9. However, a drug that cannot be dissolved in the solvent of the lipid solution to be used in the preparation of the O/W type emulsion may render the encapsulation operation difficult. Therefore, as the combination of a hardly water-soluble drug and the solvent of the lipid solution to be used in the present invention, a hardly water-soluble drug having solubility (25° C.) of preferably not less than 1 mM, more preferably not less than 5 mM, is used.

In a preferable embodiment, as a hardly water-soluble drug, a drug having an active site (target molecule) for expression of the efficacy in a cell is used.

Lipids and surfactants constituting the O/W type emulsion of the present invention are not included in the "hardly water-soluble drug".

A hardly water-soluble drug can be introduced and released into an object cell in vivo and/or in vitro by contacting the O/W type emulsion of the present invention encapsulating the hardly water-soluble drug with cells. The present invention also provides such delivery method of a hardly water-soluble drug into cells.

The kind of the cell is not particularly limited and a prokaryotic or eucaryotic cell can be used, with preference given to eucaryote. The kind of the eukaryotic cell is not particularly limited and, for example, vertebrates such as mammals including human (e.g., human, monkey, mouse, rat, hamster, bovine etc.), birds (e.g., chicken, ostrich etc.), amphibia (e.g., frog etc.), fishes (e.g., zebrafish, Oryzias latipes etc.) and the like, invertebrates such as insects (silkworm, moth, Drosophila etc.) and the like, plants, microorganisms (e.g., yeast etc.) and the like can be mentioned. More preferably, the target cell in the present invention is an animal or plant cell, more preferably a mammalian cell. The cell may be a culture cell line including a cancer cell, or a cell isolated from an individual or tissue, or a cell of a tissue or tissue piece. The cell may be an adherent cell or a non-adherent cell.

The step of contacting the O/W type emulsion of the present invention encapsulating a hardly water-soluble drug with the cell outside the body (in vitro) specifically explained below.

The cells are suspended in a suitable medium several days before contact with the O/W type emulsion, and cultured under appropriate conditions. At the time of contact with the O/W type emulsion, the cells may or may not be in a proliferative phase.

The culture medium on contact may be a serum-containing medium or a serum-free medium.

The cell density on contact is not particularly limited, and can be appropriately determined in consideration of the kind of the cell and the like. It is generally within the range of $1 \times 10^4$-$1 \times 10^7$ cells/mL.

The O/W type emulsion of the present invention encapsulating the aforementioned hardly water-soluble drug is added to the thus-prepared cells. The amount of the suspension to be added is not particularly limited, and can be appropriately determined in consideration of the cell number and the like. The concentration of the O/W type emulsion to be contacted with the cells is not particularly limited as long as the desired introduction of the hardly water-soluble drug into the cells can be achieved. The lipid concentration is generally 1-10 nmol/ml, preferably 10-50 nmol/ml.

The aforementioned suspension is added to the cells and the cells are cultured. The temperature, humidity, $CO_2$ concentration and the like in culturing are appropriately determined in consideration of the kind of the cell. When the cells are derived from mammal, generally, the temperature is about 37° C., the humidity is about 95% and the $CO_2$ concentration is about 5%. While the culture time can also be appropriately determined in consideration of the conditions such as the kind of the cell and the like, it is generally 0.1-24 hr, preferably 0.2-4 hr, more preferably 0.5-2 hr. When the above-mentioned culture time is too short, the hardly water-soluble drug is not sufficiently introduced into the cells, and when the culture time is too long, the cell may become weak.

By the above-mentioned culture, the hardly water-soluble drug is introduced into cells. The culture is further continued preferably by exchanging the medium with a fresh medium, or adding a fresh medium to the medium. When the cell is a mammal-derived cell, the fresh medium preferably contains a serum or nutrition factor.

As mentioned above, a hardly water-soluble drug can be introduced into cells not only outside the body (in vitro) but also in the body (in vivo) by using the O/W type emulsion of the present invention. That is, by administration of the O/W type emulsion of the present invention encapsulating the hardly water-soluble drug to a subject, the O/W type emulsion reaches and contacts with the target cells, and the hardly water-soluble drug encapsulated in the O/W type emulsion is introduced into the cells in vivo. The subject to which the O/W type emulsion can be administered is not particularly limited and, for example, vertebrates such as mammals (e.g., human, monkey, mouse, rat, hamster, bovine etc.), birds (e.g., chicken, ostrich etc.), amphibia (e.g., frog etc.), fishes (e.g., zebrafish, rice-fish etc.) and the like, invertebrates such as insects (e.g., silk moth, moth, Drosophila etc.) and the like, plants and the like can be mentioned. The subject of administration of the O/W type emulsion of the present invention is preferably human or other mammal.

The kind of the target cell is not particularly limited, and a hardly water-soluble drug can be introduced into cells in various tissues (e.g., liver, kidney, pancreas, lung, spleen, heart, blood, muscle, bone, brain, stomach, small intestine, large intestine, skin, adipose tissue etc.) by using the O/W type emulsion of the present invention.

The O/W type emulsion of the present invention can be efficiently delivered to a deep part of tissues such as tumor and the like by setting the volume median diameter to not more than 100 nm. Therefore, it is advantageous for delivering a hardly water-soluble drug (e.g., hardly water-soluble antitumor agent) to a tumor cell in a tumor tissue (e.g., solid tumor tissue).

An O/W type emulsion of the present invention containing B-2-5 as the compound of the formula (1) is superior in accumulation in the liver. Therefore, it is advantageous for delivering a hardly water-soluble drug (e.g., hardly water-soluble therapeutic agent for liver disorders) to a cell (e.g., hepatocyte) in a hepatic tissue.

The administration method of the O/W type emulsion encapsulating a hardly water-soluble drug of the present invention to the target (e.g., vertebrates, invertebrates and the like) is not particularly limited as long as the O/W type emulsion reaches and contacts the target cells, and the hardly water-soluble drug encapsulated in the O/W type emulsion can be introduced into the cells, and an administration method known per se (e.g., oral administration, parenteral administration (e.g., intravenous administration, intramuscular administration, topical administration, transdermal administration, subcutaneous administration, intraperitoneal administration, spray etc.) etc.) can be appropriately selected in consideration of the kind of the hardly water-soluble drug, the kind and the site of the target cell and the like. The dose of the O/W type emulsion is not particularly limited as long as the introduction of the hardly water-soluble drug into the cells can be achieved, and can be appropriately selected in consideration of the kind of the subject of administration, administration method, the kind of the hardly water-soluble drug, the kind and the site of the target cell and the like.

When the O/W type emulsion of the present invention is used as a carrier for delivering a hardly water-soluble drug into cells, it can be formulated according to a conventional method.

When the carrier is provided as a reagent for studies, the carrier of the present invention is provided the O/W type emulsion of the present invention as it is or as a suspension with, for example, water or other physiologically acceptable liquid (e.g., water-soluble solvent (e.g., malic acid buffer etc.), organic solvent (e.g., ethanol, methanol, DMSO and the like), or a mixture of aqueous solvent and organic solvent etc.). The carrier of the present invention can appropriately contain physiologically acceptable additive (e.g., excipient, vehicle, preservative, stabilizer, binder etc.), which are known per se.

When the carrier is provide as a medicament, the carrier of the present invention can use the O/W type emulsion of the present invention as it is or may be produced as an oral preparation (for example, tablet, capsule etc.) or parenteral agent (for example, injection, spray etc.), preferably parenteral agent (more preferably, injection) by blending the carrier with a pharmaceutically acceptable known additives such as carrier, flavor, excipient, vehicle, preservative, stabilizer, binder and the like in a conventionally admitted unit dosage form required for practicing preparation formulation.

The contents disclosed in any publication stated in the present specification, including patents, patent applications and scientific literatures, are hereby incorporated in their entireties by reference, to the extent that they have been disclosed herein.

The Examples of the present invention are explained in further detail in the following, but the present invention is not limited in any way by the Examples.

EXAMPLES

[Example 1] Preparation of Fine O/W Type Emulsion

Using B-2, B-2-5, O-C3M, B-2-3, TS-P4C2 or L-PZ4C2 as a cationic lipid, an O/W type emulsion having a composition of cationic lipid:DOPE:Cholesterol=3:4:3 (molar ratio) was prepared. In this preparation, 4-Methylumbelliferon (10 mol %) was used as a model drug and DMG-PEG2000 (10 mol %) and DSG-PEG2000 (2.5 mol %) were used as PEG lipids, and a 1.0 mM (based on lipid concentration) emulsion was prepared.

An ethanol solution containing 1000 nmol as a total of cationic lipid, DOPE, and Cholesterol was prepared, and a model drug and PEG lipid were added in the above-mentioned amounts. Ethanol was added to make the total amount 400 μL, and the mixture was stood at ice temperature for 15 min. A similarly ice-cooled malic acid buffer (20 mM, pH 3.0, 30 mM NaCl) (400 μL) was mixed within 3 sec under vortex. PBS (NISSUI) (3200 μL) was immediately added thereto. The mixture was subjected to ultrafiltration using Amicon Ultra (Millipore). The centrifugation conditions were 1000 g, 25° C. An operation including addition of 3200 μL of PBS after centrifugation for 10 min was repeated twice and the sample was concentrated to about 500 μL. The concentrate was diluted with PBS to a mass of 1000 mg to give a 1 mM (based on lipid concentration) emulsion.

The particle size distribution of the prepared emulsion was measured by dynamic light scattering using Zetasizer Nano ZS. The measurement conditions were 1 mM emulsion (40 μL) at 25° C. As a result, in all compositions, the volume median diameter was not more than 100 nm and, when a linear head was used (i.e., the formula (I) wherein $X^a$ and $X^b$ are each $X^1$), the particle size was not more than 50 nm. The drug recovery rate was not less than 85% (FIG. 1, Table 2).

TABLE 2

| cationic lipid | volume median diameter (nm) | PdI | drug recovery rate (%) |
|---|---|---|---|
| B-2 | 37.6 | 0.465 | 92.3 |
| B-2-5 | 41.2 | 0.164 | 85.0 |
| O-C3M | 38.4 | 0.228 | 95.5 |
| B-2-3 | 34.3 | 0.419 | 90.7 |
| TS-P4C2 | 87.9 | 0.063 | 95.1 |
| L-PZ4C2 | 75.8 | 0.092 | 89.1 |

[Comparative Example 1] Preparation Using Conventional Lipid DODAP and EPC

Using DODAP as a cationic lipid, particles having a composition of DODAP:DOPE:Cholesterol=3:4:3 (molar ratio) was prepared. In this preparation, 4-Methylumbelliferon (10 mol %) was used as a model drug and DMG-PEG2000 (10 mol %) and DSG-PEG2000 (2.5 mol %) were used as PEG lipids, and a 1.0 mM (based on lipid concentration) particle suspension was prepared. Preparation of the particles and obtainment of the particle size distribution were performed according to the method described in Example 1.

Using EPC as a neutral lipid, particles having a composition of EPC:Cholesterol=3:2 were prepared. In this preparation, 4-Methylumbelliferon (10 mol %) was used as a model drug and DSG-PEG2000 (2.5 mol %) was used as a PEG lipid, and a 1.0 mM (based on lipid concentration) particle suspension was prepared.

EPC and Cholesterol were mixed to achieve 1000 nmol and a PEG lipid was added. Chloroform in an amount equal to that of the lipid ethanol solution was added and the mixture was dried under a nitrogen blow. PBS (1 mL) was added to the lipid membrane after drying and the mixture was stood for 10 min and sonicated by a bath-type sonicator for 3 min to give a particle suspension. The particle size distribution of the prepared particles was measured by dynamic light scattering in the same manner as in Example 1.

Figure 2:
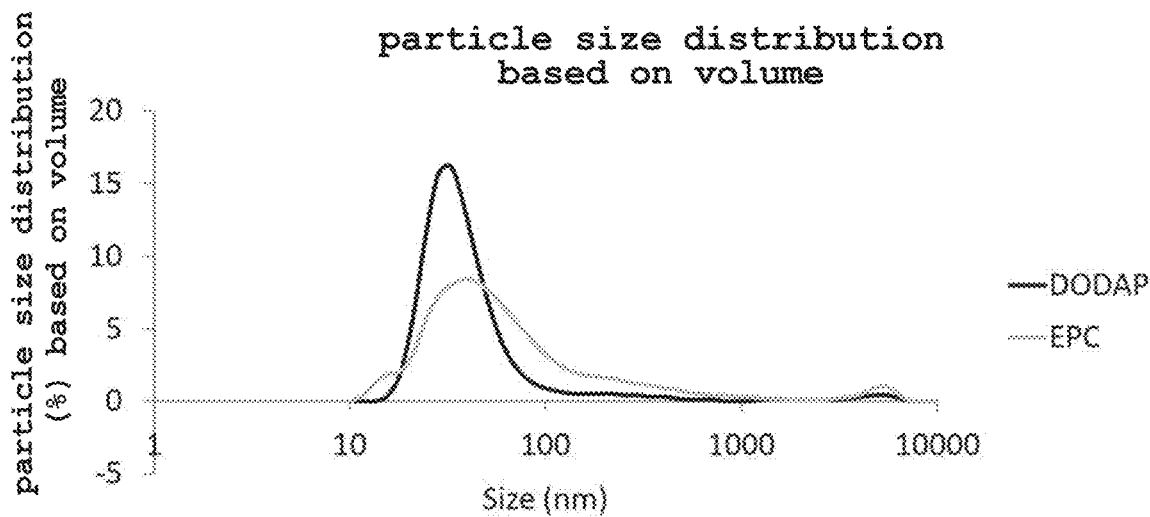
FIG. 2 shows particle size distribution based on the volume of various particle suspensions prepared from DODAP or EPC.

As a result, the volume median diameter of DODAP was 34.8 nm, PdI was 0.418 and the model drug recovery rate was 76.7%. The volume median diameter of EPC was 48.1 nm and an aggregate was found by visual observation (FIG. 2, Table 3).

TABLE 3

| lipid | volume median diameter (nm) | PdI | drug recovery rate (%) | note |
|---|---|---|---|---|
| DODAP | 34.8 | 0.418 | 76.7 | |
| EPC | 48.1 | 0.384 | 101 | coarse aggregate was observed |

[Example 2] Influence of pH on O/W Type Emulsion

Using B-2 as a cationic lipid, an O/W type emulsion having a composition of cationic lipid:DOPE:Cholesterol=3:4:3 (molar ratio) or cationic lipid:DOPC:Cholesterol=3:4:3 (molar ratio) was prepared. In this preparation, 15 mol % DMG-PEG2000 was used as a PEG lipid and a 0.5 mM (based on lipid concentration) emulsion was prepared.

An ethanol solution containing 500 nmol as a total of B-2, DOPE, and Cholesterol was prepared, and a PEG lipid was added in the above-mentioned amount. Ethanol was added to make the total amount 200 μL, and the mixture was stood at ice temperature for 15 min. A similarly ice-cooled malic acid buffer (20 mM, pH 3.0-pH 5.0) (200 μL) was mixed within 3 sec under vortex. PBS (NISSUI) (3600 μL) was immediately added thereto. The mixture was subjected to ultrafiltration using Amicon Ultra (Millipore). The centrifugation conditions were 1000 G, 25° C. An operation including addition of 3200 μL of PBS after centrifugation for 10 min was repeated twice and the sample was concentrated to about 500 μL. The concentrate was diluted with PBS to a mass of 1000 mg to give a 0.5 mM emulsion solution.

Figure 3:
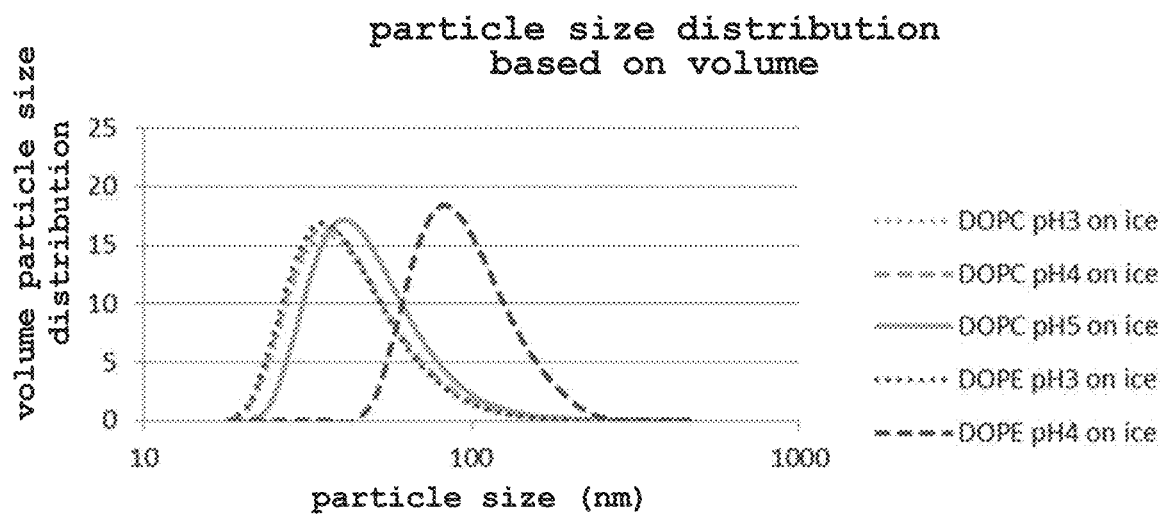
FIG. 3 shows an influence, on the particle size, of the pH at the time of preparation of emulsions containing DOPC or DOPE in addition to B-2 and cholesterol.

The particle size distribution of the produced emulsion solution was measured by dynamic light scattering similarly to Example 1. As a result, when DOPC was used, the volume median diameter was near 40 nm irrespective of pH. When DOPE was used, the volume median diameter showed pH dependency and the smallest particles of about 40 nm were obtained at pH 3.0. Therefore, as the condition for forming fine particles, pH 3.0 was superior (FIG. 3, Table 4).

TABLE 4

| helper lipid | pH | volume median diameter (nm) | PdI |
|---|---|---|---|
| DOPE | 3.0 | 39.5 | 0.191 |
| DOPE | 4.0 | 90.2 | 0.078 |
| DOPC | 3.0 | 41.5 | 0.319 |
| DOPC | 4.0 | 40.5 | 0.214 |
| DOPC | 5.0 | 45.6 | 0.196 |

[Example 3] Influence of Salt Concentration on B-2 O/W Type Emulsion

Using B-2 as a cationic lipid, an O/W type emulsion having a composition of cationic lipid:DOPE:Cholesterol=3:4:3 (molar ratio) was prepared. In this preparation, 15 mol % DMG-PEG2000 was used as a PEG lipid and a 0.5 mM (based on lipid concentration) emulsion was prepared.

An ethanol solution containing 500 nmol as a total of cationic B-2, DOPE, and Cholesterol was prepared, and a PEG lipid was added in the above-mentioned amount. Ethanol was added to make the total amount 200 μL, and the mixture was stood at ice temperature for 15 min. A similarly ice-cooled malic acid buffer (20 mM, pH 3.0, 0-1000 mM NaCl) (200 μL) was mixed within 3 sec under vortex. PBS (NISSUI) (3600 μL) was immediately added thereto. The mixture was subjected to ultrafiltration using Amicon Ultra (Millipore). The centrifugation conditions were 1000 G, 25° C. An operation including addition of 3200 μL of PBS after centrifugation for 10 min was repeated twice and the sample was concentrated to about 500 μL. The concentrate was diluted with PBS to a mass of 1000 mg to give a 0.5 mM (lipid concentration) emulsion. The particle size distribution of the produced emulsion solution was measured by dynamic light scattering similarly to Example 1.

Figure 4:
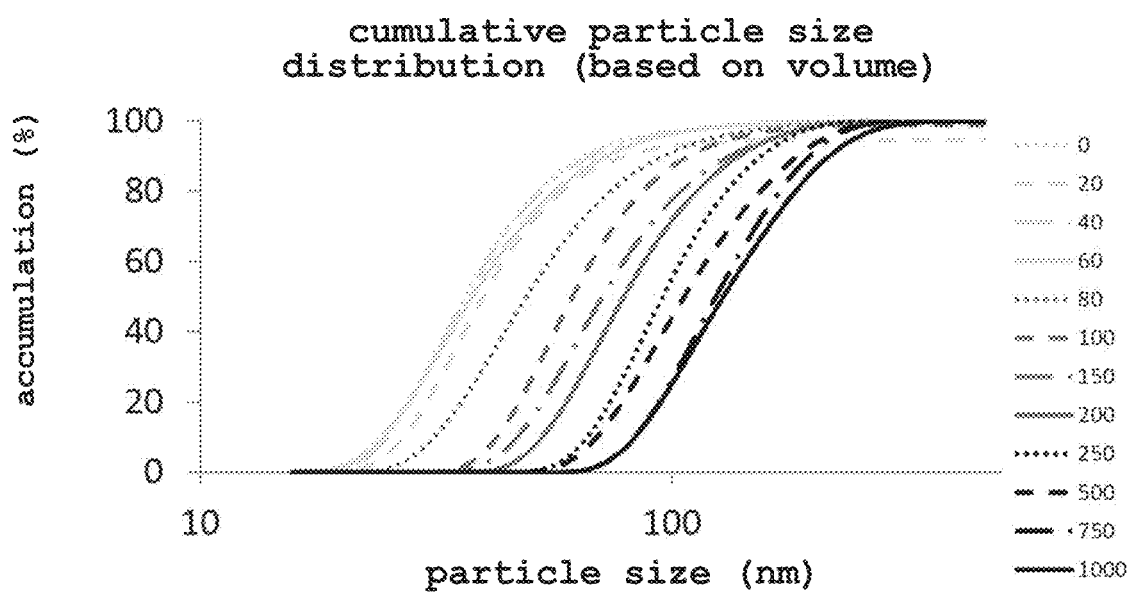
FIG. 4 shows an influence, on the particle size distribution, of the salt concentration at the time of preparation of emulsions containing B-2, DOPE, and cholesterol.
Figure 5:
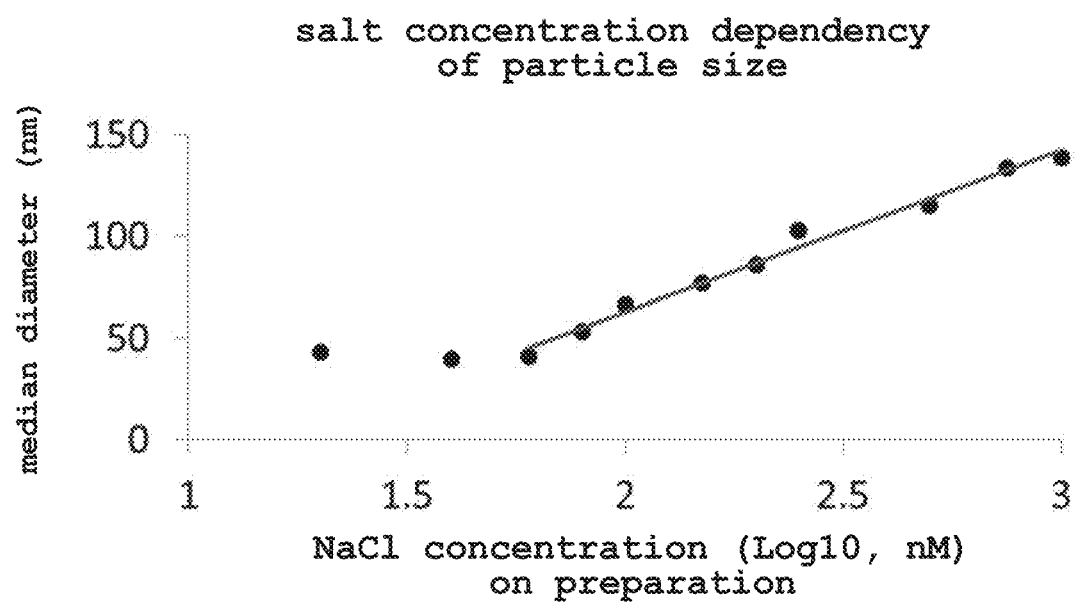
FIG. 5 shows the relationship between the salt concentration and volume median diameter at the time of preparation of emulsions containing B-2, DOPE and cholesterol.

As a result, the volume median diameter was shown to be 30-50 nm at NaCl concentration of 60 mM or below. At a salt concentration of 500 mM or below, the volume median diameter was shown to be controllable to 100 nm or below (FIG. 4, FIG. 5).

[Example 4] Drug Release and Reduction Responsibility Test

Using B-2, B-2-5, O-C3M, B-2-3, TS-P4C2 or L-PZ4C2 as a cationic lipid, an O/W type emulsion having a composition of cationic lipid:DOPC:Cholesterol=3:4:3 (molar ratio) was prepared. In this preparation, DSG-PEG2000 (9 mol %) was used as a PEG lipid. As a drug model molecule, 4-Methylumbelliferon Palmitate (30 mol %) was used and fluorescent probe DiD (1 mol %) was used for calibration by particles concentration.

An ethanol solution containing 1000 nmol as a total of cationic lipid, DOPE, and Cholesterol was prepared, and PEG lipid, drug model molecule and fluorescent probe were added in the above-mentioned amounts. Ethanol was added to make the total amount 400 μL, and the mixture was stood at 37° C. for 15 min. A similarly heated malic acid buffer (20 mM, pH 3.0, 30 mM NaCl) (400 μL) was mixed within 3 sec under vortex. PBS (NISSUI) (3200 μL) was immediately added thereto. The mixture was subjected to ultrafiltration using Amicon Ultra (Millipore) The centrifugation conditions were 1000 g, 25° C. An operation including addition of 3200 μL of PBS after centrifugation for 10 min was repeated twice and the sample was concentrated to about 500 μL. The concentrate was diluted with PBS to a mass of 1000 mg to give a 1 mM (based on lipid concentration) emulsion.

400 μL of the prepared emulsion was placed in a dialysis membrane (Spectrum Lab) having a molecular weight cutoff of 1000 and dialyzed against 40 mL of PBS at 37° C. In this case, to examine responsiveness under reduction, 40 mL of PBS containing 10 mM glutathione was also dialyzed similarly. 30 μL of the solution in the dialysis tube was collected at each time point. The collected sample was diluted 3-fold with PBS, and 5 μL was mixed with 300 μL of borate buffer (100 mM, pH 10.4), 150 μL of ethanol, and 50 μL of 10% SDS (total 505 μL). After penetration and stirring at 60° C. for 30 min, the amounts of 4MU and DiD in the solution were quantified by fluorescence measurement (4MU: Ex385, Em450 DiD: Ex645, Em665). The residual amount of 4MU was divided by the residual amount of DiD and used as the drug residual amount relative to the particles.

Figure 6:
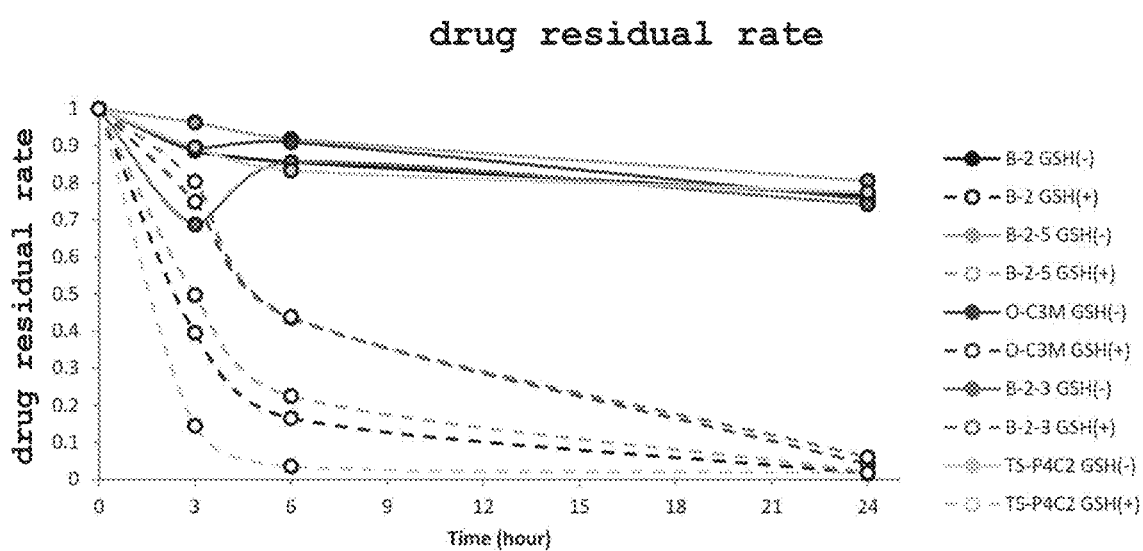
FIG. 6 shows drug release under reduction condition or nonreduction environment from various emulsions prepared from B-2, B-2-5, O-C3M, B-2-3 or TS-P4C2.
Figure 14:
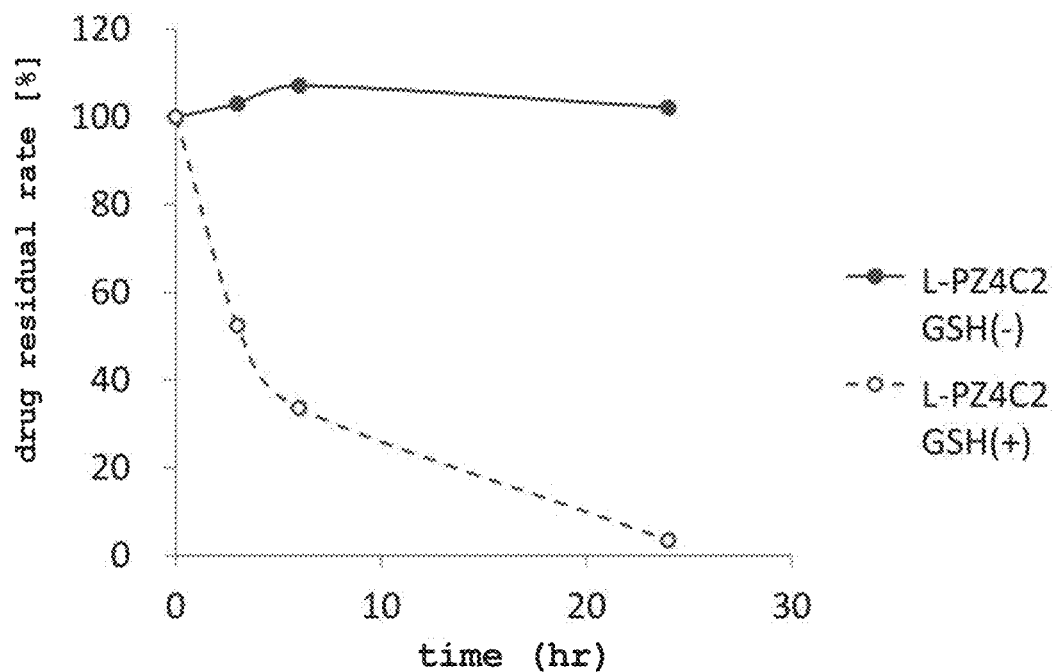
FIG. 14 shows drug release under reduction condition (GSH(+)) and under nonreduction environment (GSH(-)) from an emulsion prepared from L-PZ4C2.

As a result, the O/W type emulsion stably maintained the drug for 24 hr under the nonreduction environment, whereas almost complete drug release was found under reduction condition in 24 hr (FIG. 6, FIG. 14). Therefrom it was considered that the O/W type emulsion has drug releaseability under reductive environment in the cell.

[Comparative Example 2] Drug Release and Reduction Responsibility Test (DODAP, EPC)

Using DODAP or EPC as a conventional lipid, a particle suspension having a composition of conventional lipid:DOPC:Cholesterol=3:4:3 (molar ratio) was prepared. In this preparation, 9 mol % DMG-PEG2000 was used as a PEG lipid. As a drug model molecule, 30 mol % 4-Methylumbelliferon Palmitate was used, and 1 mol % fluorescent probe DiD was used for calibration by particle concentration.

Preparation and drug release test of the particles were performed by the method described in Example 3.

Figure 7:
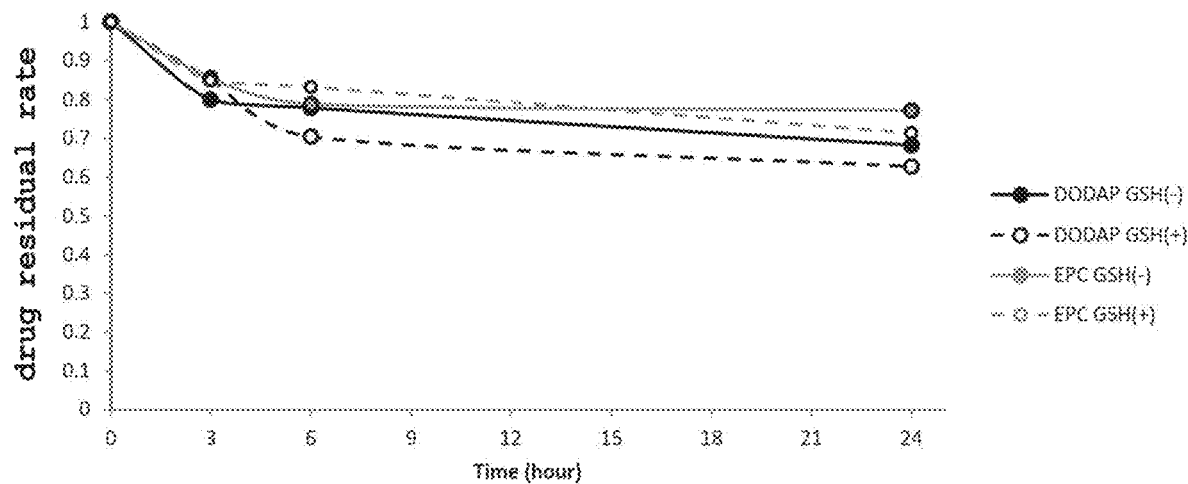
FIG. 7 shows drug release under reduction condition or nonreduction environment from various particle suspensions prepared from DODAP or EPC.

As a result, responsiveness under reduction was not found and the drug model substance was hardly released for 24 hr under any conditions (FIG. 7).

[Experimental Example 1] Organ Accumulation of O/W Type Emulsion Particles

As cationic lipid, B-2 and B-2-5 were used. As conventional lipid, DODAP and EPC were used. The preparation methods of the O/W type emulsion and particle suspensions (DODAP, EPC) followed the methods described in Example 1 and Comparative Example 1. To visualize pharmacokinetics of the oil droplets constituting the O/W type emulsion or particle suspension (DODAP, EPC), fluorescent dye DiR was added by 0.2 mol % of the lipid. The particle concentration was adjusted to 4 mM as a lipid concentration.

As a tumor-bearing mouse, 4T1 cell (mouse breast cancer) was used. $1 \times 10^6$ 4T1 cells were subcutaneously transplanted to the right flank of BALB/c mouse (♀, 4-week-old). At 7 days from the transplantation, 200 μL (lipid 800 nmol) of the O/W type emulsion or particle suspension (DODAP, EPC) containing fluorescence-modified particles was intravenously administered. At 24 hr after administration, liver hemorrhage was performed, and the spleen, liver and tumor were collected and image was obtained by IVIS. The average fluorescence intensity was calculated using Living Image Software.

Figure 8:
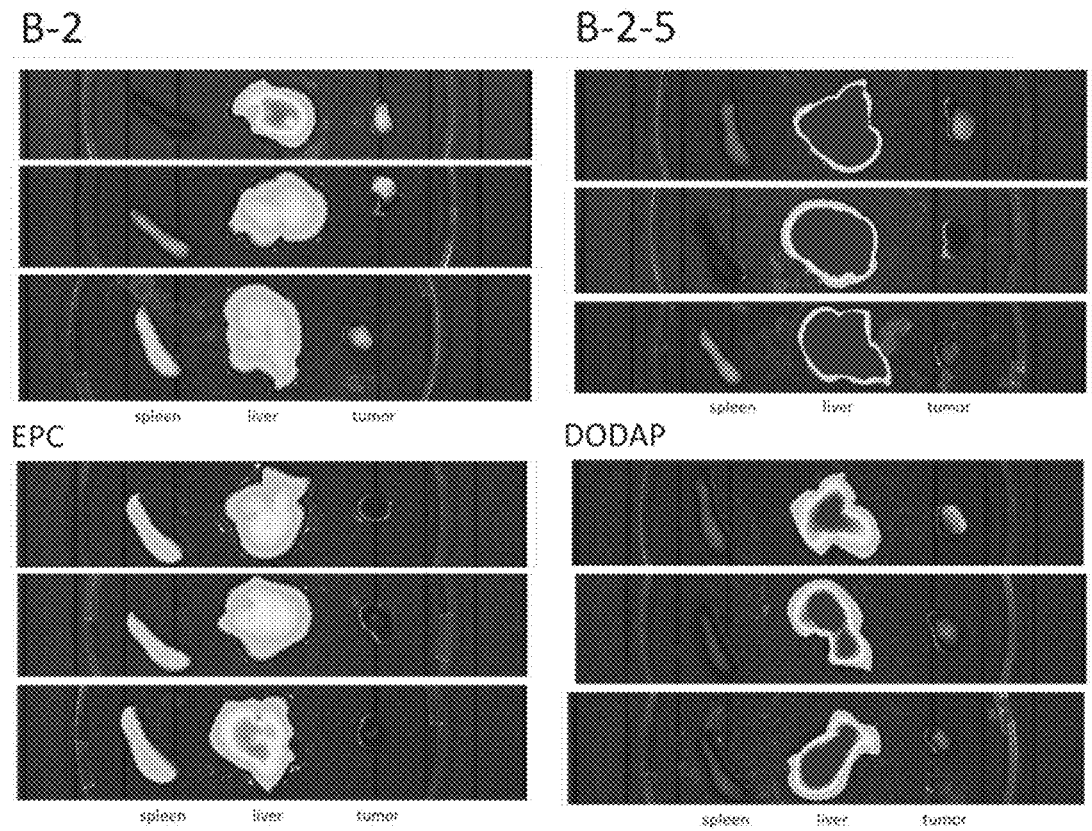
FIG. 8 shows major organ distribution of particles (oil droplets) when various emulsions and particle suspensions prepared from B-2, B-2-5, EPC or DODAP were intravenously injected.
Figure 9:
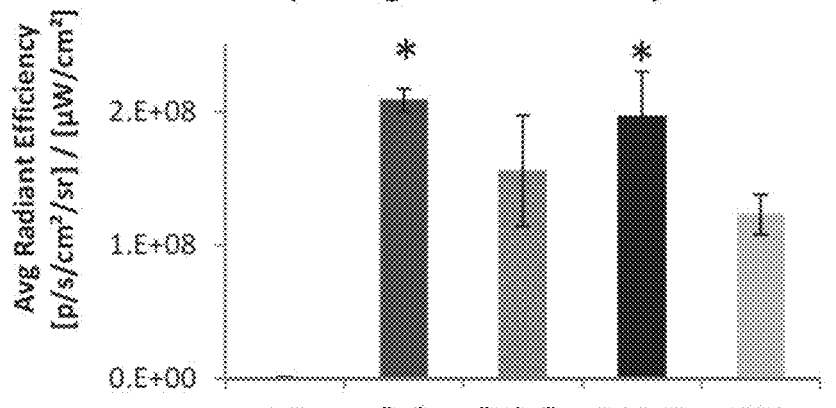
FIG. 9 shows quantitative evaluation of the major organ distribution shown in FIG. 8.
Figure 9:
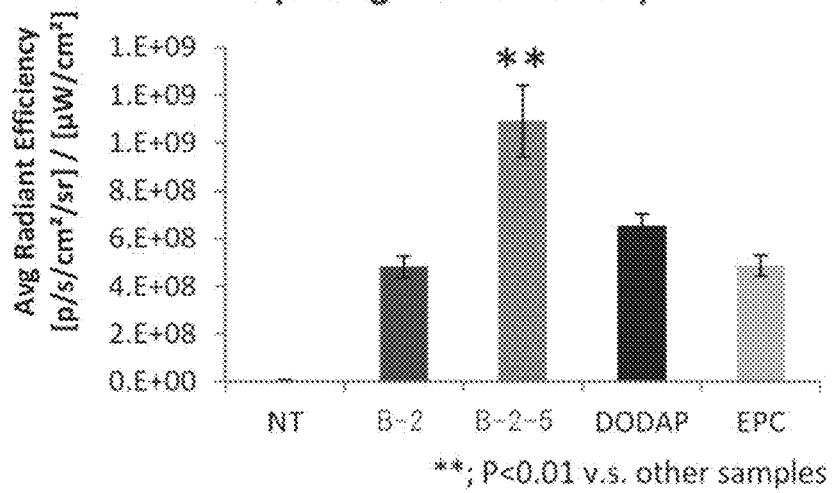
Figure 9:
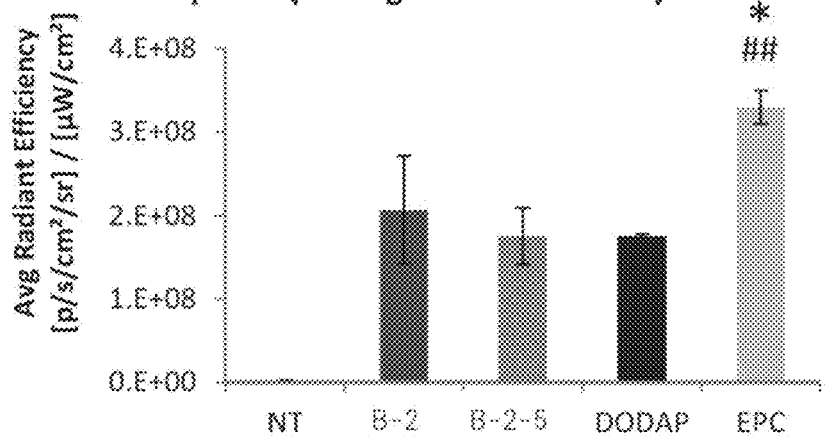

As a result, accumulation of B-2-5 in the liver was found. Accumulation of EPC in the spleen was found and contribution to coarse aggregate was considered. It was shown that B-2 and DODAP transfer well into tumor (FIGS. 8, 9).

[Experimental Example 2] Particle Size Dependency of Tumor-Cumulative O/W Type Emulsion As a cationic lipid, B-2 was used. An O/W type emulsion was prepared according to Example 3. In this preparation, 4-Methylumbelliferon (10 mol %) was used as a model drug and DMG-PEG2000 (10 mol %) and DSG-PEG2000 (2.5 mol %) were used as PEG lipids, and a 4.0 mM (based on lipid concentration) emulsion was prepared. To visualize pharmacokinetics of the oil droplets constituting the O/W type emulsion or particle suspension (DODAP, EPC), fluorescent dye DiR was added by 0.2 mol % of the lipid. As the salt (NaCl) concentration during preparation of particles, 30 mM, 150 mM, 750 mM were selected and taken as "Small", "Medium", "Large", respectively. The particle concentration was adjusted to 4 mM as a lipid concentration.

Figure 10:
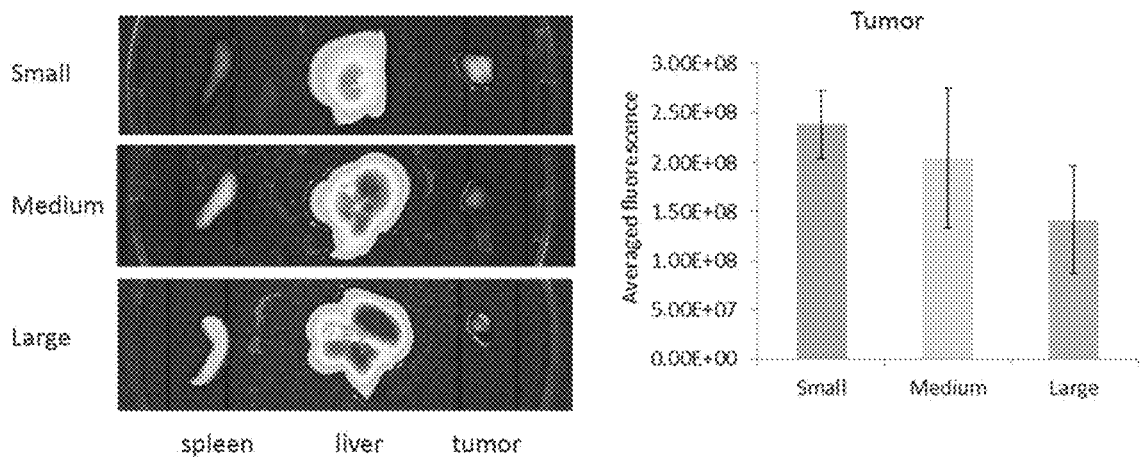
FIG. 10 shows an influence of particle size on the tumor accumulation by the emulsion prepared from B-2.

The organ distribution in a tumor-bearing mouse was evaluated in the same manner as in Experimental Example 1. As a result, accumulation in the spleen, liver decreased as the particle size became smaller. On the other hand, when the particle size became smaller, accumulation in tumor increased and particles showing the highest accumulation were "Small". Therefrom it was suggested that fine O/W type emulsion is suitable for drug delivery into tumor (FIG. 10).

[Experimental Example 3] Intratumor Particles Distribution

As cationic lipid, B-2 and B-2-5 were used. As conventional lipid, DODAP and EPC were used. The O/W type emulsion and particle suspensions (DODAP, EPC) were produced by the methods described in Example 1 and Comparative Example 1. To visualize pharmacokinetics of the oil droplets constituting the O/W type emulsion or particle suspension (DODAP, EPC), fluorescent dye DiD was added by 1.0% of the lipid. The particle concentration was adjusted to 4 mM as a lipid concentration.

Preparation of the tumor-bearing mouse and intravenous administration were performed in the same manner as in Experimental Example 1. At 24 hr after the administration, the tumor was collected and a 400 μm-thick section was produced with a microslicer. The fluorescence of DiD was obtained by a confocal laser scan microscope (Nikon A-1). The image was obtained using a ×10 lens as a large image of the whole tumor. The image was quantified by ImageJ. Coefficiency of variance (CV; index of nonuniformity in image) was calculated by dividing the dispersion of the whole pixel intensity by the mean of pixel intensity.

Figure 11:
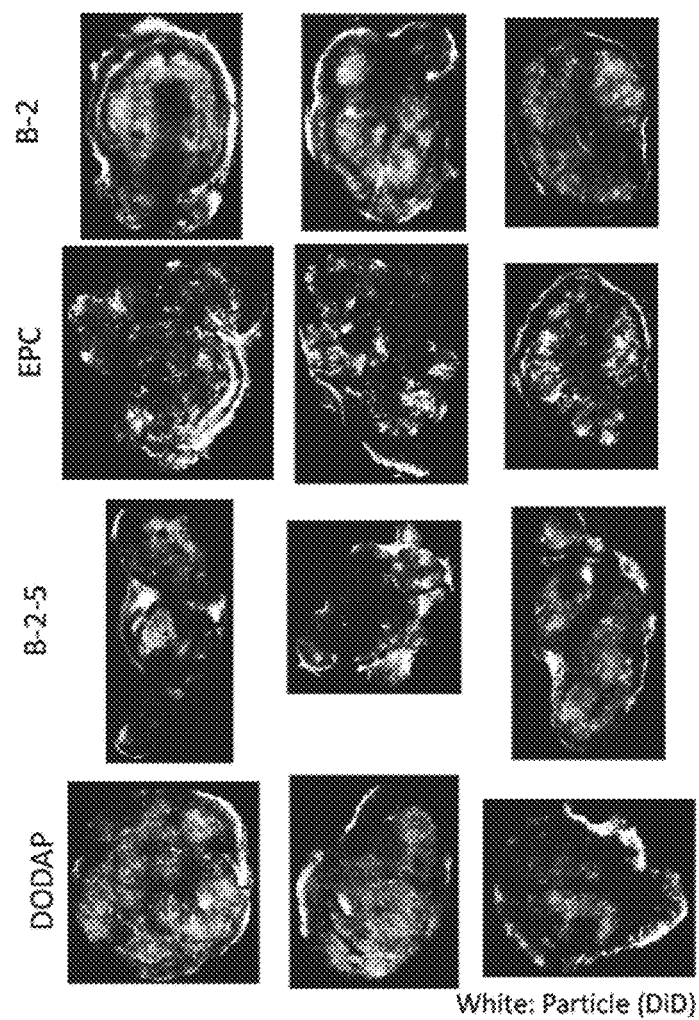
FIG. 11 shows fluorescence microscopic images of intratumoral distribution of various particles (oil droplets) prepared from B-2, B-2-5, DODAP or EPC.
Figure 12:
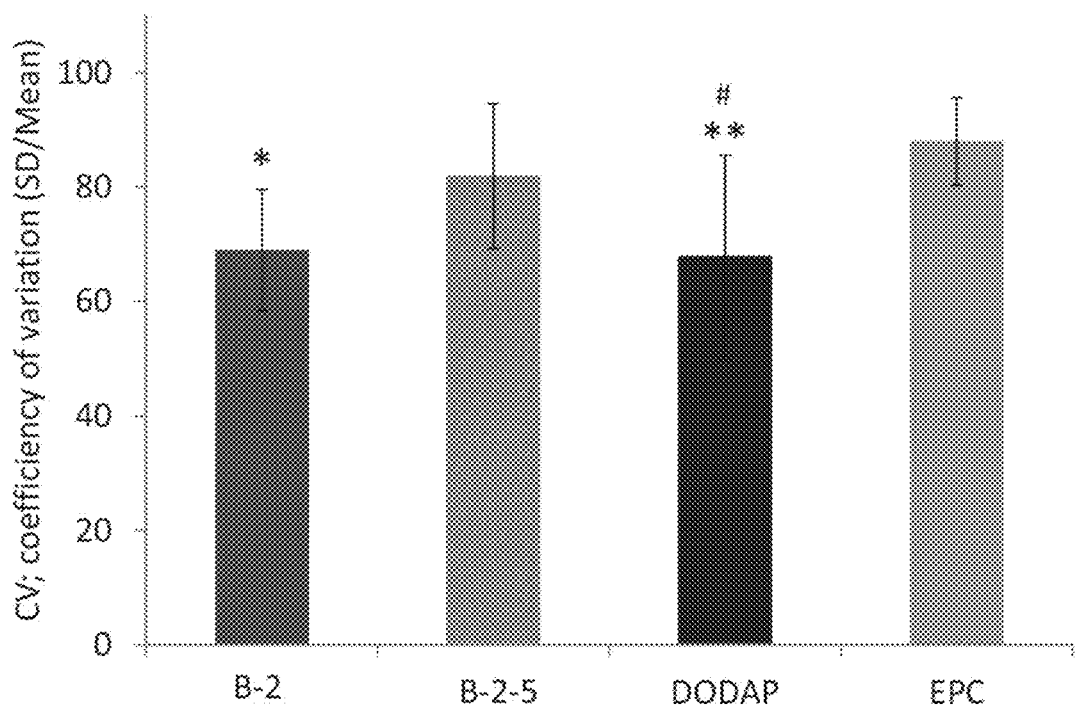
FIG. 12 shows quantified non-uniformity of intratumoral distribution of various particles (oil droplets) prepared from B-2, B-2-5, DODAP or EPC.

As a result, it was clarified that B-2 and DODAP have low CV value, which shows nonuniformity of image. This was considered to result from improved penetration into the tumor due to microscaling of the particles (FIG. 11, FIG. 12).

[Experimental Example 4] Antitumor Effect of Dexamethasone Palmitate (DexPal)-Carrying Particles 1. Preparation of DexPal-Carrying Particles Using B-2 or DODAP as a cationic lipid and, as an ethanol solution of lipid, 5 mM cationic lipid (60 μL), 5 mM DOPC (80 μL), 5 mM Chol (60 μL), 1 mM DMG-PEG2000 (100 μL), 1 mM DSG-PEG2000 (30 μL) and 10 mM DexPal (30 μL) were mixed in a 5 mL tube, and ethanol was added to 400 μL. Using EPC as a neutral lipid, 5 mM EPC (140 μL), 5 mM Chol (60 μL), 1 mM DMG-PEG2000 (100 μL), 1 mM DSG-PEG2000 (30 μL) and 10 mM DexPal (30 μL) were mixed in a 5 mL tube, and ethanol was added to 400 μL. The lipid ethanol solution was stood on ice for 10 min. While stirring the lipid ethanol solution, ice-cooled 20 mM malic acid buffer (pH 3.0, 30 mM NaCl) (400 μL) was added, and the mixture was stirred for several seconds. Then, ice-cooled phosphate buffer (pH 7.4) (2000 μL) was added, and the mixture was stirred for several seconds. Phosphate buffer (pH 7.4) (1200 μL) was added, and the mixture was concentrated to about 500 μL by repeated ultrafiltration using Amicon Ultra 4 (Millipore) under the following centrifugation conditions (room temperature, 1000 g, 3 min). Phosphate buffer (pH 7.4) (4000 μL) was added, and the mixture was concentrated to about 500 μL again by ultrafiltration under the same conditions. This operation was repeated again. The concentrate was diluted with phosphate buffer (pH 7.4) to 1000 μL in a measuring cylinder to give an O/W type emulsion and a particle suspension each containing 1 mM DexPal-carrying particles (oil droplets).

2. Measurement of Particle Size, and Surface Potential of DexPal-Carrying Particles The volume median diameter and the surface potential were measured using the dynamic light scattering (Zetasizer Nano; Malvern) in the same manner as in Example 1. The volume median diameter and surface potential of the various particles prepared are shown in Table 5.

TABLE 5

| | volume median diameter (d · nm) | PdI |
| --- | --- | --- |
| B-2 | 41.4 ± 0.7 | 0.15 ± 0.01 |
| DODAP | 39.1 ± 2.2 | 0.15 ± 0.01 |
| EPC | 44.8 ± 0.8 | 0.15 ± 0.01 |

3. Measurement of DexPal-Carrying Rate of DexPal-Carrying LNP 1 mM DexPal-carrying LNP (50 μL) was mixed with phosphate buffer (pH 7.4) (50 μL), and 50 μL thereof was mixed with MeOH (50 μL). 0.1% Trifluoroacetic acid/acetonitrile (400 μL) was added, and DexPal was detected by high performance liquid chromatography (column: Inert-Sustain C18, 5 μm, 4.6 mm×250 mm (GL Sciences Inc.), mobile phase: MeOH:0.1% trifluoroacetic acid/acetonitrile=70:30, flow rate: 1 mL/min, detector: 240 nm, injection volume: 200 μL). As the analytical curve of Dex-Pal, 0.5 mM, 0.25 mM, 0.125 mM, 0.0625 mM, DexPalethanol solution (50 μL) was mixed with MeOH (50 μL), and 50 μL thereof was mixed with phosphate buffer (pH 7.4) (50 μL). 0.1% Trifluoroacetic acid/acetonitrile (400 μL) was added, and DexPal was detected by a method similar to that for DexPal-carrying LNP. The peak area and concentration were plotted, and the DexPal concentration and carrying rate in the DexPal-carrying LNP were calculated. The carrying rates of various DexPal-carrying LNPs are shown in Table 6.

TABLE 6

| | carrying rate (%) |
| --- | --- |
| B-2 | 90.6 ± 5.2 |
| DODAP | 89.6 ± 2.9 |
| EPC | 90.5 ± 4.0 |

4. Verification of Antitumor Effect of DexPal-Carrying LNP on EG7-OVA Lymphoma

Figure 13:
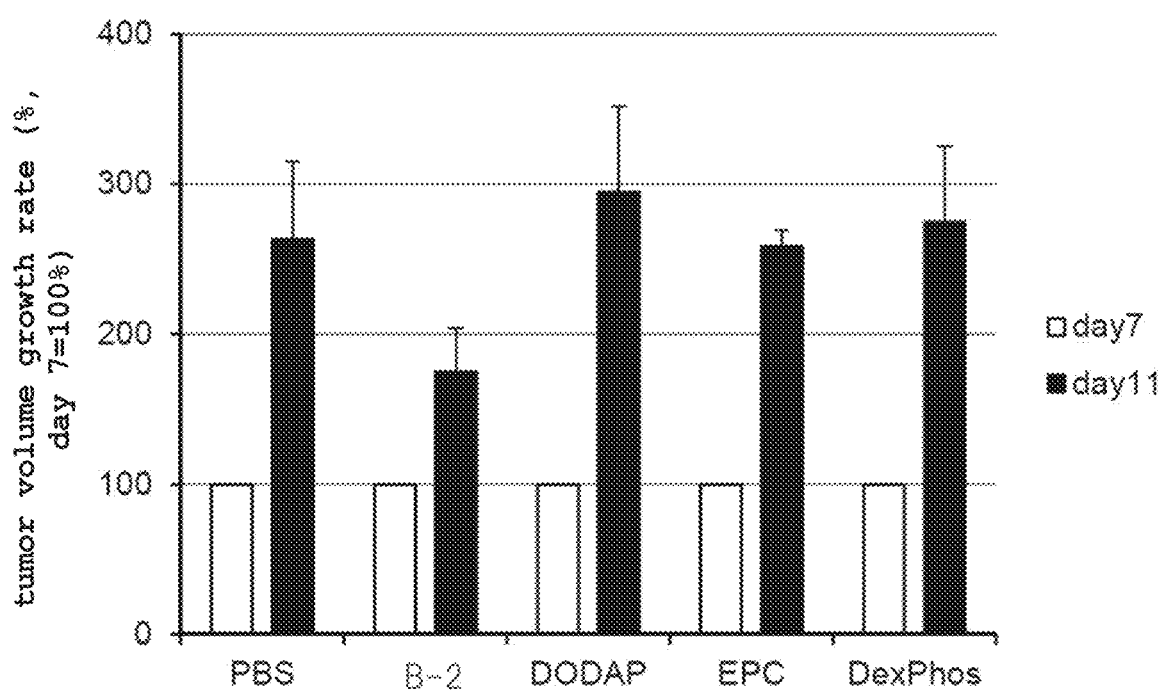
FIG. 13 shows the tumor volume growth rate of the group administered with various particles prepared from B-2, DODAP or EPC and the comparison control group.

EG7-OVA (OVA-expressing EL4 lymphoma) ($8.0 \times 10^5$ cells) was subcutaneously transplanted to the right flank of C57BL/6L (6- to 8-week-old, ♀) and, one week later, the tumor volume was calculated according to the following formula: (major axis (mm³))×(minor axis (mm³))²×0.52). Tumor-bearing mice having a tumor volume of 100-200 mm³ were randomly divided into groups. After 24 hr, Dex-Pal-carrying LNP containing B-2, DODAP or EPC, which was prepared as mentioned above, and Dexamethasone Sodium Phosphate (DexPhos) as a water-soluble Dexamethasone preparation were administered from the tail vein at 1 mg/mL based on Dexamethasone. After 24 hr and 48 hr, similar DexPal-carrying LNP and DexPhos were administered, and the tumor volume was calculated at 24 hr after the final administration. The ratio of the tumor volume at 24 hr from the final administration when the tumor volume at 1 week after the transplantation was 100% is shown in FIG. 13.

[Example 5] Production of 4-Methylumbelliferone Cholesterol Hemisuccinate (4MU-CHEMS), Dexamethasone Cholesterol Hemisuccinate (Dex-CHEMS)-Containing O/W Type Emulsions 1. Production of 4MU-CHEMS-Containing O/W Type Emulsion To B-2:DOPC:Chol=3:4:3 were added 9 mol % DSG-PEG2000 and 30 mol % 4MU-CHEMS, and 1 mol % fluorescent dye DiD was further added to give an emulsion similar to that in Example 1.

2. Production of Dex-CHEMS-Containing O/W Type Emulsion

An emulsion having lipid composition: B-2/DOPC/Chol=3/4/3, 10 mol % Dex-CHEMS, 10 mol % DMG-PEG2000 and 3 mol % DSG-PEG2000 was produced by a method similar to that in Example 1.

The average particle size of the produced particles was measured in the same manner as in Example 1 and the results are shown in Table 7.

TABLE 7

|  | volume median diameter (nm) |
| --- | --- |
| 4MU-CHEMS-containing emulsion | 53.4 |
| Dex-CHEMS-containing emulsion | 49.2 |

[Experimental Example 5] Retentivity in Blood Test: Comparison of 4-Methylumbelliferone Palmitate (4 MU-Pal) and 4-Methylumbelliferone Cholesterol Hemisuccinate (4 MU-CHEMS)

To a lipid mixture of B-2:DOPC:Chol=3:4:3 were added DSG-PEG2000 (9 mol %) and 30 mol % 4 MU-Pal, and 1 mol % fluorescent dye DiD was added to give an emulsion by a method similar to that in Example 1.

To a lipid mixture of B-2:DOPC:Chol:4 MU-CHEMS=3:4:1.5:1.5 was added DSG-PEG2000 (15 mol %), fluorescent dye DiD (1 mol %) was further added, and an emulsion was prepared by a method similar to that in Example 1.

Figure 15:
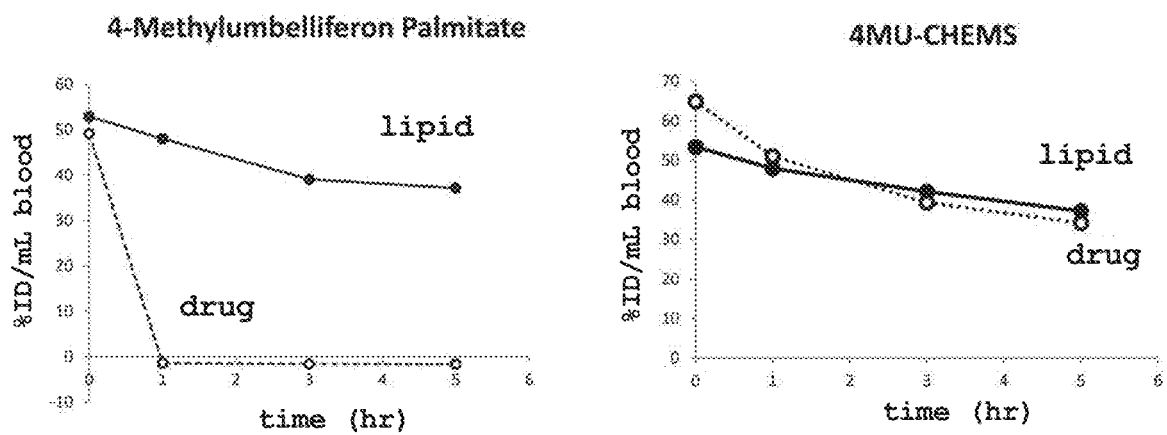
FIG. 15 shows a comparison of retentivities in blood of lipid and a drug in emulsions prepared from B-2 and 4-methylumbelliferone palmitate or 4-methylumbelliferone cholesterol hemisuccinate.

The concentration of the particle suspension was set to 4 mM as a lipid concentration (B-2+DOPC+Chol). The suspension (250 µL) was administered to ICR mouse J 4-week-old from the tail vein. Blood (25 µL) was collected at each time point and mixed with pH 10.4 borate buffer (275 µL), ethanol (150 µL), 10% SDS (50 µL). 4 MU-Pal or 4 MU-CHEMS was hydrolyzed by incubation at 60° C. for 30 min. The fluorescence of the resulting 4-methylumbelliferone, and DiD modified by particles was each measured by a plate reader and the residual amount in the blood was examined from the analytical curve. The results are shown in FIG. 15. 4 MU-CHEMS stayed longer in the blood than 4 MU-Pal.

[Experimental Example 6] Retentivity in Blood Test: Comparison of 4 MU-CHEMS in Tumor and Blood Concentration To a lipid mixture of B-2:DOPC:4 MU-CHEMS=3:4:3 was added DSG-PEG2000 (20 mol %) and particles were prepared. The concentration of the particle suspension was set to 8 mM as a lipid concentration. To BALB/c mouse (♀ 4-week-old, transplantation 7 days) subcutaneously transplanted with 4T1 cells was administered 200 µL from the tail vein. The retentivity in blood was examined similarly to Experimental Example 5. As for concentration in tumor, tumor was collected at each time point, collected tumor was chopped and then 25 mg was measured. Borate buffer (pH 10.4, 300 µL), ethanol (150 µL) and 10% SDS (50 µL) were added and the mixture was homogenized. The homogenate was incubated at 60° C. for 30 min, and centrifuged at 14000 g for 5 min. The fluorescence intensity of the supernatant was examined and the existing amount was estimated from the analytical curve.

Figure 16:
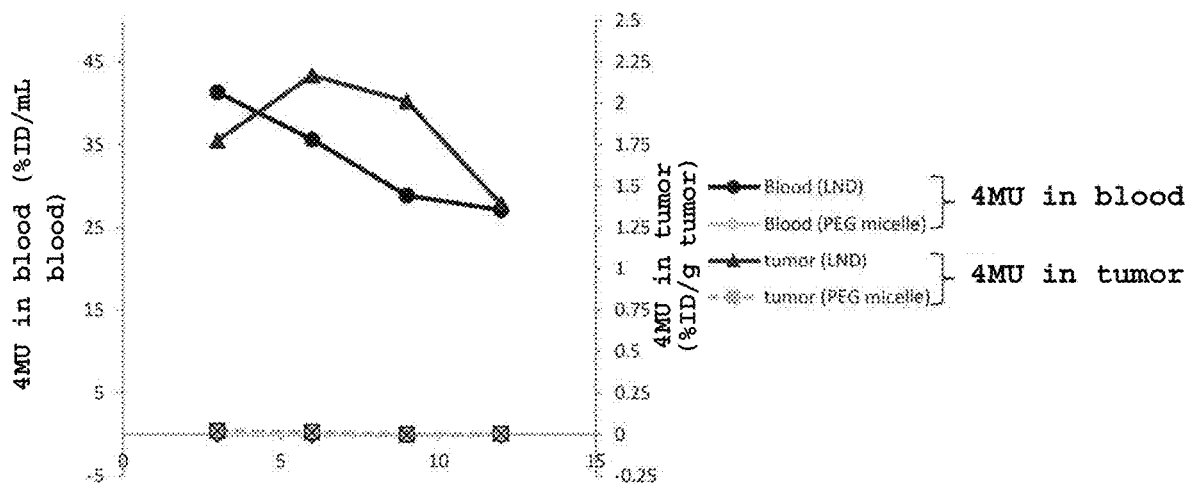
FIG. 16 shows a comparison of drug concentration in blood and drug concentration in tumor in emulsions prepared from B-2 and 4-methylumbelliferone cholesterol hemi succinate.

As the comparison target, a micelle composed of 4-methylumbelliferone and DSG-PEG2000 was used. The micelle was prepared to contain 1.6 mM DSG-PEG2000 and 2.4 mM 4 MU in PBS containing 2% DMSO. Administration and quantification were performed in the same manner as in the particles. The results are shown in FIG. 16. The emulsion composed of B-2 and 4 MU-CHEMS stayed loner in blood as compared to the micelle composed of 4-methylumbelliferone and DSG-PEG2000, and accumulated in tumor.

[Experimental Example 7] Organ Distribution of 4 MU-CHEMS-Containing Emulsion

Figure 17:
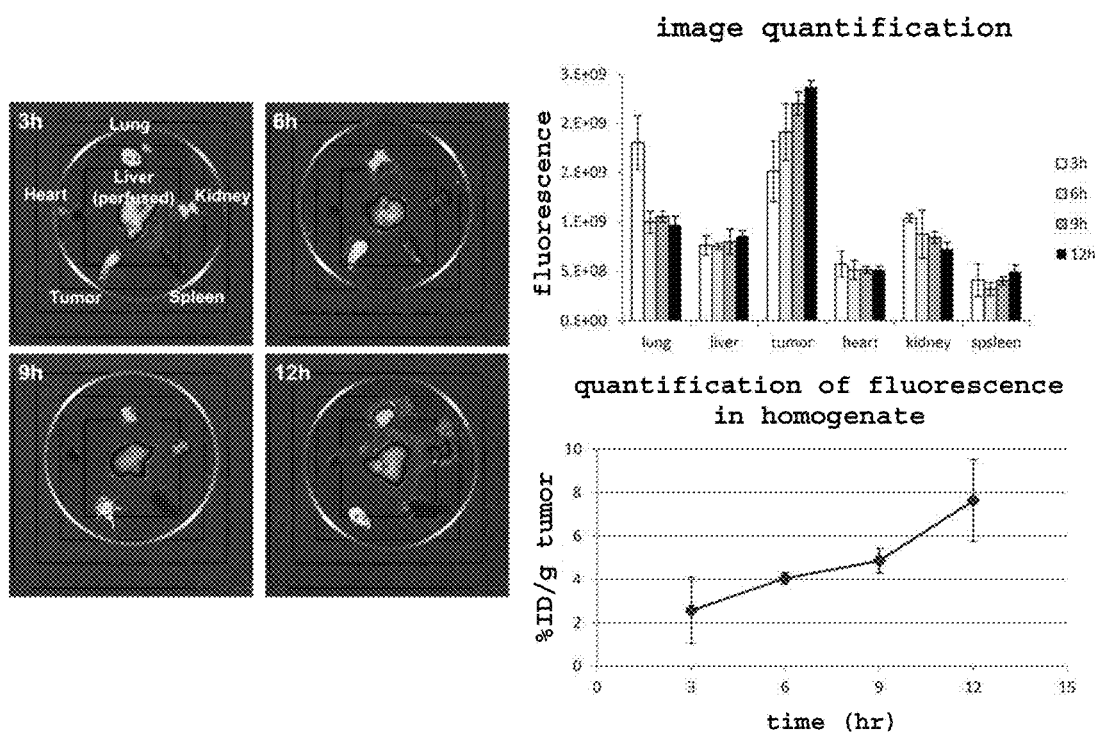
FIG. 17 shows a comparison of organ distributions of emulsions prepared from B-2 and 4 methylumbelliferone cholesterol hemisuccinate.

To B-2:DOPC:4 MU-CHEMS=3:4:3 was added 20 mol % DSG-PEG2000, 1 mol % fluorescent dye DiD was added, and an emulsion was prepared in the same manner as in Example 1. The particle suspension was adjusted to 8 mM as a lipid concentration and 200 µL was administered from the tail vein to BALB/c mouse (Y 4-week-old) subcutaneously transplanted with 4T1 cells. The liver was hemorrhaged with heparin/PBS, the liver, lung, heart, kidney, spleen, tumor were removed, and fluorescence of DiD was obtained by IVIS. In addition, average pixel intensity relating to each organ was calculated. Each tumor was chopped and 25 mg was measured. After homogenizing with Triton/PBS, the homogenate was centrifuged, and the fluorescence of DiD contained in the supernatant was obtained by a plate reader. The results are shown in FIG. 17. The emulsion composed of B-2 and 4 MU-CHEMS accumulated in tumor and the amount of accumulation increased over time.

[Experimental Example 8] Evaluation of Retentivity in Blood

1. Preparation of Emulsion Composed of Dexamethasone Cholesterol Hemisuccinate (Dex-CHEMS) and B-2

When the lipid composition was 3 mM B-2/DOPC/Chol=3/4/3+10 mol % Dex-CHEMS+10 mol % DMG-PEG2000+10 mol % DSG-PEG2000 (1000 µL), a lipid solution was mixed in vitro as follows.

TABLE 8

| | |
|---|---|
| 20 mM B-2 in EtOH | 45 μL |
| 20 mM DOPC in EtOH | 60 μL |
| 20 mM Chol in EtOH | 45 μL |
| 10 mM DMG-PEG2000 in EtOH | 30 μL |
| 10 mM DSG-PEG2000 in EtOH | 9 μL |
| 5 mM Dex-CHEMS in CHCl$_3$:EtOH = 9:1 | 60 μL |

The solvent was evaporated once and the residue was redissolved in 100 μL CHCl$_3$. N$_2$ gas was blown to form a lipid thin film on the wall of a test tube. After a few hours of a vacuum treatment by a desiccator, 20 mM Maric acid buffer (30 mM NaCl, pH 3.0, 1000 μL) was added, and the mixture was incubated for 10 min at room temperature. After sonication with a bath-type sonicator for 30 sec, the mixture was sonicated by a probe-type sonicator for 5 min (output power: 30%). After centrifugation at 4° C., 15000 g for 5 min, the supernatant was collected. Neutralization was performed by adding an equal amount of 36 mM NaOH/PBS.

2. Quantification of Dex-CHEMS

Respective particles (100 μL) were transferred to a 1.5 mL tube and dried by a concentrator (Heat:High) for 30 min. The particles were dissolved in 0.1% TFA/Hexane:0.1% TFA/EtOH=9:1 (100 μL), and the recovery rate was calculated by HPLC and using the peak area of Dex-CHEMS (HPLC conditions . . . mobile phase: 0.1% TFA/Hexane: 0.1% TFA/EtOH=9:1, column: COSMOSIL SL-II, flow rate: 1 mL/min, analysis time: 10 min, column temperature: 40° C., detection wavelength: 240 nm, peak of Dex-CHEMS: 3.90 min). In addition, as the analytical curve of Dex-CHEMS, 0.5, 0.25, 0.125, 0.0625 mM Dex-CHEMS in 0.1% TFA/Hexane:0.1% TFA/EtOH:CHCl$_3$=8:1:1 was used.

3. Administration, Blood Collection

An emulsion composed of Dex-CHEMS and B-2 was administered to ICR mouse (4 w ♂) at 25 μg Dex-CHEMS/mouse. Using a 26 G injection needle, 40 μL of blood was collected from the tail vein at 1 min, 1 hr, 6 hr, 24 hr after the administration, quickly added to a PCR tube containing 1 μL of 5000 U/mL heparin sodium, blended by tapping and preserved on ice.

4. Measurement of Dex-CHEMS

Plasma (16.5 μL) centrifuged at 4° C., 1000 g for 10 min was transferred to another 1.5 mL tube. DDW was added to 50 μL, CHCl$_3$ (62.5 μL) and 0.04 mM 4-methylumbelliferone palmitate (4 MU-Pal) in MeOH (using 4 MU-Pal as standard substance) (125 μL) were added and the mixture was vortexed for about 30 sec. CHCl$_3$ (62.5 μL) and DDW (62.5 μL) were added, the mixture was vortexed for 30 sec and centrifuged at 4° C., 15000 g for 5 min. CHCl$_3$ (100 μL) in the lower layer was collected in another tube, the solvent was evaporated and the residue was dissolved in 0.1% TFA/Hexane:0.1% TFA/EtOH=9:1 (100 μL). Using HPLC, the peak area of Dex-CHEMS and the peak area of 4 MU-Pal were calculated. The peak area of 0.5, 0.25, 0.125, 0.0625 nmol Dex-CHEMS was calculated by a similar method using HPLC and used as an analytical curve.

(HPLC conditions: mobile phase: 0.1% TFA/Hexane: 0.1% TFA/EtOH=9:1, column: COSMOSIL SL-II, flow rate: 1 mL/min, analysis time: 10 min, column temperature: 40° C., detection wavelength: 240 nm (Dex-CHEMS) or 280 nm (4 MU-Pal), Dex-CHEMS: 3.90 min, peak of 4 MU-Pal: 3.27 min).

Figure 18:
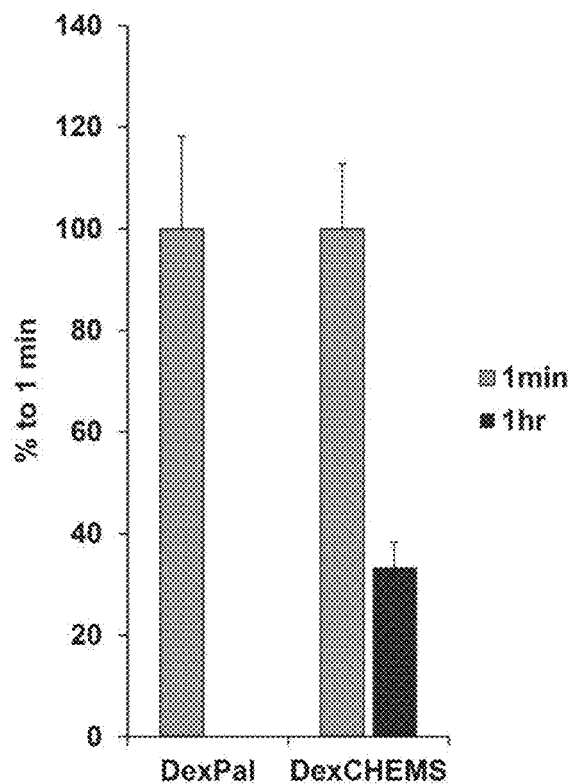
FIG. 18 shows a comparison of retentivities in blood of a drug in emulsions composed of B-2 and dexamethasone palmitate or dexamethasone cholesterol hemisuccinate.

The residual rate in blood at 1 hr later was calculated with that 1 min after the administration as 100%. The results are shown in FIG. 18. Similar to the above-mentioned, an emulsion composed of B-2 and dexamethasone palmitate (Dex-Pal) was prepared and evaluated similarly. As a result, Dex-Pal disappeared from blood 1 hr later, whereas Dex-CHEMS continuously remained.

[Experimental Example 9] Influence of Concentration of PEG Lipid

Figure 19:
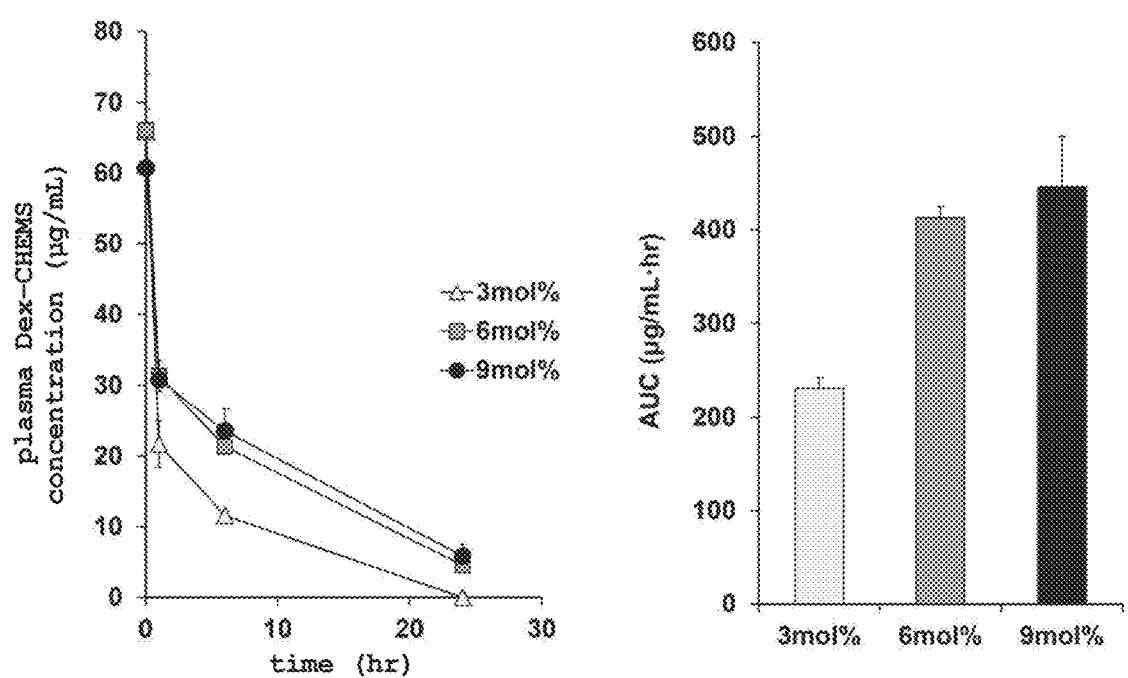
FIG. 19 shows a comparison of retentivities in blood at various PEG lipid concentrations of an emulsion composed of B-2 and dexamethasone cholesterol hemisuccinate.

An emulsion having a composition of B-2/DOPC/Chol=3/4/3+10 mol % DMG-PEG2000+3-9 mol % DSG-PEG2000+10 mol % Dex-CHEMS was prepared in the same manner as in Example 1. An emulsion having each PEG amount was administered from the mouse tail vein, plasma was collected 1 min, 1 hr, 6 hr and 24 hr later, extracted with an organic solvent, and Dex-CHEMS concentration was calculated by HPLC. The results are shown in FIG. 19. Along with an increase in DSG-PEG2000, the retentivity in blood was improved to become almost equal for DSG-PEG2000 6 mol % and 9 mol %.

[Experimental Example 10] mRNA Expression Evaluation

1. Production of Emulsion

An emulsion having a composition of B-2/DOPC/Chol=3/4/3+10 mol % DMG-PEG2000+6 mol % DSG-PEG2000+10 mol % Dex-CHEMS was prepared in the same manner as in Example 1.

2. Tumor mRNA Extraction

Tumor-bearing mouse was euthanized by cervical dislocation, tumor was isolated with scissors for anatomy, the skin was removed and chopped in a petri dish on ice. About 50 mg of tumor was placed in a self-standing 2 mL tube containing zirconia beads and rapidly frozen with liquid nitrogen. All samples were isolated, taken out from liquid nitrogen, added with 500 μL of TRIzol, and subjected to a crushing treatment using Microsmash (4800 rpm, 30 sec, 2 times). 100 μL of chloroform was added and the mixture was vortexed for 1 min and stood for 5 min. The tube was centrifuged at 4° C., 12000 g for 15 min, the supernatant (200 μL) was transferred to a 1.5 mL tube and 250 μL of isopropanol was added. After vortexing for 1 min, and the mixture was stood for 5 min and centrifuged at 4° C., 12000 g for 15 min, and the supernatant was removed. 500 μL of ice-cooled 70% ethanol was added, the pellets were floated and centrifuged at 4° C., 12000 g for 10 min, and the supernatant was removed. This operation was performed again, and the pellets were completely dissolved in 100 μL of RNase free water. 250 μL of ethanol and 5 μL of 5 M NaCl were added, and the mixture was vortexed for 1 min, stood for 5 min and centrifuged at 4° C., 12000 g for 15 min, and the supernatant was removed. 500 μL of ice-cooled 70% ethanol was added, the pellets were floated and centrifuged at 4° C., 12000 g for 10 min, and the supernatant was removed. The pellets were completely dissolved in 500 μL of RNase free water, and the concentration was measured from the absorbance.

3. Reverse Transcription Reaction

The reaction was performed with the following composition.

TABLE 9

| | |
|---|---|
| total RNA | 0.25 μg |
| 4 × DN Master Mix (with gDNA remover) | 2 μL |
| 5 × RT Master Mix II | 2 μL |
| DNase/RNase free water | |
| total | 10 μL |

A thermal cycler was turned on, the protocol was initiated and pre-incubation of the cap was performed (105° C.). Total RNA was placed in a PCR tube at 0.25 μg/6 μL, and modified under the conditions of 65° C., 5 min→4° C., ∞.

4×DN Master Mix (with gDNA remover, 2 μL) was added, and the mixture was gently stirred and reacted under the conditions of 37° C., 5 min→4° C., ∞.

5×RT Master Mix II (2 μL) was added, and the mixture was gently stirred and reacted under the conditions of 37° C., 15 min→50° C., 5 min→98° C., 5 min→4° C., ∞.

The mixture was diluted 10-fold in another PCR tube, and preserved at 4° C. when used within 24 hr and preserved at −20° C. in other cases.

4. Quantitatively Real-Time PCR

Quantitatively real-time PCR was performed using THUNDERBIRD (registered trade mark) SYBR (registered trade mark) qPCR Mix (TOYOBO), and Light Cycler 480 (Roche Diagnostics) and a 384 well plate. The reagents were mixed to achieve the following composition per 1 well.

TABLE 10

| THUNDERBIRD (registered trade mark) SYBR (registered trade mark) qPCR Mix | 2.5 μL |
|---|---|
| 20 μM Forward primer | 0.125 μL |
| 20 μM Reverse primer | 0.125 μL |
| cDNA | 0.95 μL |
| DDW | 1.3 μL |

All measurements were performed in duplicate. The reaction conditions were as follows. Analysis was performed by the ddCt method.

TABLE 11

| Pre-incubation | 95° C., 1 min (4.80° C./sec) |
|---|---|
| Amplification | 95° C., 15 sec (4.80° C./sec) |
|  | →55° C., 30 sec (2.50° C./sec) |
|  | →60° C., 30 sec (4.80° C./sec) |
|  | (40 cycle) |
| Melting Curve | 95° C., 5 sec (4.80° C./sec) |
|  | →65° C., 1 min (2.50° C./sec) |
|  | →97° C., (0.11° C./sec) |
| Cooling | 40° C., 15 sec (2.50° C./sec) |

Figure 20:
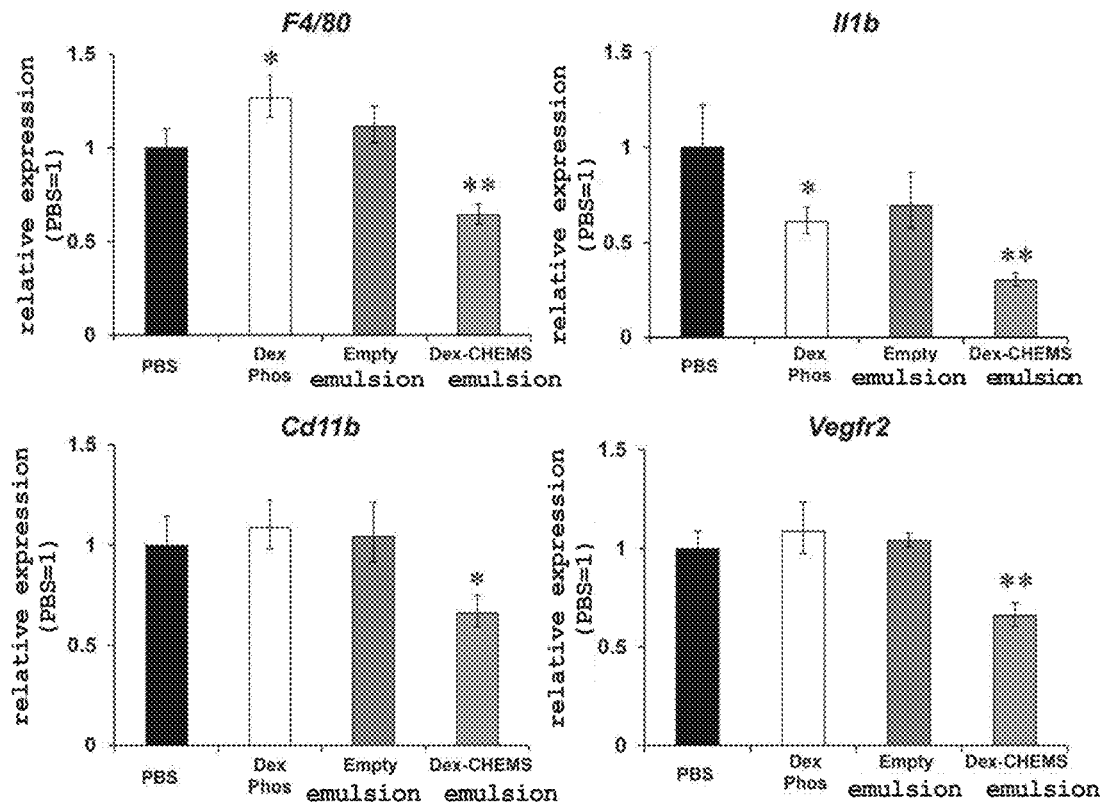
FIG. 20 shows evaluation of the expression level of various mRNAs when an emulsion composed of B-2 and dexamethasone cholesterol hemisuccinate was administered to mouse.

An emulsion composed of B-2 and Dex-CHEMS, PBS as comparison and, Dexamethasone Sodium Phosphate (Dex-Phos) as water-soluble Dexamethasone preparation, and an emulsion obtained by removing Dex-CHEMS from an emulsion composed of B-2 and Dex-CHEMS were administered and compared with the value in PBS as 1. The results are shown in FIG. 20. In all indices, the emulsion composed of B-2 and Dex-CHEMS showed the lowest values.

[Experimental Example 11] Antitumor Effect

1. Tumor Transplantation

EG7-OVA seeded at $5.0 \times 10^5$ cells/dish two days before were collected and washed twice with 10 mL of PBS. The cells were counted and suspended in PBS at $8.0 \times 10^5$ cells/40 μL. The suspension was administered at $8.0 \times 10^5$ cells/40 μL to the right flank of C57BL/6J (6- to 8-week-old, ♀).

2. DC Vaccine

Bone marrow-derived dendritic cells (BMDC) induced by the following method to $1.0 \times 10^6$ cells/500 μL/well were seeded in a non-treated bottom 12 well plate.

DOPE and Phosphatidic acid were mixed in a test tube at DOPE: Phosphatidic acid=7:2 (molar ratio), and the solvent was evaporated. Equal amounts of 0.12 mg/mL of protamine solution and 0.8 mg/mL of plasmid DNA solution were mixed in a vortex mixer and a plasmid DNA/protamine particle suspension was prepared (using 10 mM HEPES buffer as a solvent). A plasmid DNA/protamine particle suspension was added in vitro such that the lipid concentration would be 0.55 mM, and the mixture was incubated at room temperature for 10 min. They were sonicated by a bath-type sonicator, and STR-KALA was mixed at 10 mol % of the total lipid amount to give KALA-modified plasmid DNA containing nanoparticles.

KALA-modified plasmid DNA containing nanoparticles was added to achieve an appropriate concentration (Serum (−), GM-CSF(+)). After 2 hr, the medium (serum(+)) was added. After 4 hr, BMDC was collected from each well, washed twice with PBS, cells were counted and diluted with PBS to achieve an appropriate cell concentration. C57BL/6J (6 w, ♀) was anesthetized with diethyl ether and 40 μL of BMDC suspension was subcutaneously administered from the back of the both paws.

3. Administration of Emulsion Composed of Dex-CHEMS and B-2

The emulsion prepared in Experimental Example 1 and composed of Dex-CHEMS and B-2 was administered from the tail vein in an amount corresponding to 0.5 mg/kg based on Dexamethasone.

The tumor volume was calculated according to the following formula.

$$\text{Tumor volume (mm}^3\text{)} = (\text{major axis (mm)}) \times (\text{minor axis (mm)})^2 \times 0.52$$

4. Induction of Mouse Bone Marrow-Derived Dendritic Cell (BMDC)

RPMI-1640 medium and PBS were each added in a sterilized petri dish by 10 mL per mouse, femur and cervical vertebra were isolated from C57BL/6J or BALB/c mice (6- to 10-week-old) subjected to cervical dislocation, lightly disinfected with 70% ethanol and immersed in PBS. The both ends of the bone were cut, and the bone marrow cells were pushed out with the medium in a 1 mL syringe (26 G needle). The cell suspension was passed through a 40 μm cell strainer and transferred to a 50 mL conical tube. After centrifugation (450 g, 4° C., 5 min), the supernatant was removed, ACK Lysing Buffer (1 mL) was added, and the mixture was mixed and stood at room temperature for 5 min. The medium (9 mL) was added, the mixture was centrifuged and the supernatant was removed. The residue was washed twice with the medium (10 mL). Then, the cells were suspended in the medium (10 mL), and the suspension was added to a 10 cm cell culture dish and cultured at 37° C., 5%, $CO_2$ conditions for not less than 4 hr. With gentle pipetting, only floating cells were collected in a 50 mL conical tube and centrifuged. The supernatant was removed, and the cells were suspended in the medium (10 mL) and counted. The cells were suspended in the medium at $1 \times 10^6$ cells/mL, GM-CSF was added (final concentration 10 ng/mL), seeded in 24 well plate by 1 mL and cultured for 2 days under 37° C., 5%, $CO_2$ conditions. Floating cells were removed 2 days later and 4 days later leaving cell aggregates. Fresh GM-CSF containing RPMI-1640 medium (1 mL) was added. Floating and weakly-adherent cells at 6 days from the start of the culture in the presence of GM-CSF were used as immature dendritic cells for the experiment.

Figure 21:
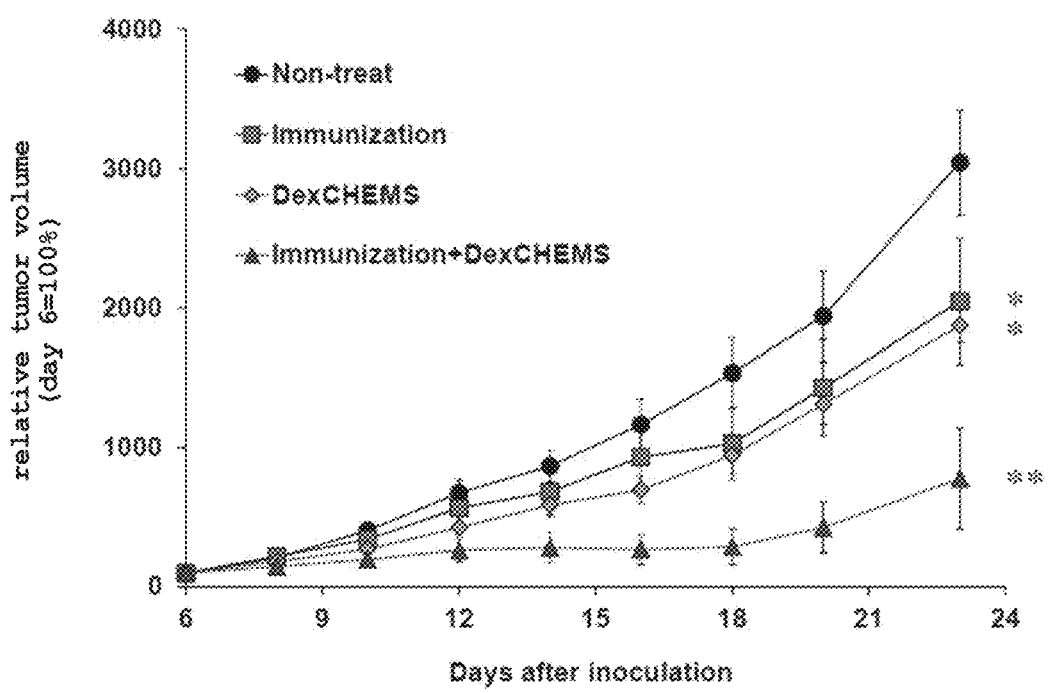
FIG. 21 shows evaluation of the antitumor effect when an emulsion composed of B-2 and dexamethasone cholesterol hemisuccinate was administered to mouse.

A comparison of nontreated (non-treat), only immunized group (immunization), a group without immunization but administered with the emulsion composed of Dex-CHEMS and B-2, which was prepared in Experimental Example 1 (Dex-CHEMS), and a group immunized and administered with the emulsion composed of Dex-CHEMS and B-2, which was prepared in Experimental Example 1 (immunization+Dex-CHEMS) is shown in FIG. 21. The group immunized and administered with the emulsion composed of Dex-CHEMS and B-2, which was prepared in Experimental Example 1 (immunization+Dex-CHEMS) showed the highest antitumor effect.

[Reference Example 1] Synthesis of TS-PZ4C2

<Mesylation>

Acetonitrile (143 mL) was added to bis(2-hydroxyethyl) disulfide (15 g, manufactured by Tokyo Chemical Industry Co., Ltd.) (97 mmol), and the mixture was dissolved at 20-25° C. Triethylamine (33.3 g, manufactured by KANTO CHEMICAL CO., INC.) (328 mmol) was added, and the mixture was cooled to 10° C. with stirring. Methanesulfonyl chloride (34.5 g, manufactured by KANTO CHEMICAL CO., INC.) (300 mmol) was added dropwise over for 1 hr to set the temperature to 20° C. or below. After the completion of the dropwise addition, the mixture was reacted at 20-25° C. for 3 hr. The disappearance of the spot of bis(2-hydroxyethyl) disulfide was confirmed by TLC analysis (eluent: chloroform, iodine color development), and the reaction was completed. Ethanol (29 mL) was added to the reaction solution to discontinue the reaction, and insoluble materials were removed by filtration. 10% Sodium bicarbonate water (150 g) was added to the filtrate, and the mixture was stirred for 5 min and stood for 10 min. The aqueous layer was removed, and the residue was purified by extracting 4 times with sodium bicarbonate water. The obtained organic layer was dehydrated with magnesium sulfate (4.5 g). Insoluble materials were removed by filtration, and the solvent in the filtrate was distilled off by an evaporator to give a brown solid (hereinafter to be referred to as "di-MS form") (29.4 g).
<1H-NMR Spectrum (600 MHz, CDCl$_3$)>

The analysis results of $^1$H-NMR spectrum of the obtained compound, di-MS form, are shown below.

δ2.95-3.20 ppm (m, C$\underline{H}_3$—SO$_2$—O—CH$_2$—CH$_2$—S—, 10H), δ4.45-4.50 ppm (t, CH$_3$—SO$_2$—O—C$\underline{H}_2$—CH$_2$—S—, 4H)

<Tertiary Amination>

Acetonitrile (31 mL) was added to the di-MS form (1.2 g, 4 mmol), and the mixture was dissolved at 20-25° C. Potassium carbonate (1.3 g, manufactured by KANTO CHEMICAL CO., INC.) (10 mmol) was added and the mixture was stirred for 5 min. Thereafter, 4-piperazineethanol (5.0 g, manufactured by Tokyo Chemical Industry Co., Ltd.) (39 mmol) was added and the mixture was reacted at 25-35° C. for 13 hr. The disappearance of the spot of the di-MS form was confirmed by TLC analysis (eluent: chloroform/methanol/28% aqueous ammonia=80/20/2(v/v/v), iodine color development), and the reaction was completed. Insoluble materials were removed by filtration, and the solvent in the filtrate was distilled off by an evaporator. The obtained brown liquid was dissolved in chloroform (25 mL), distilled water (25 mL) was added and the mixture was stirred for 5 min. After stirring, the mixture was stood for 10 min and the aqueous layer was removed. Thereafter, the residue was purified by extracting 2 times with distilled water. The obtained organic layer was dehydrated with magnesium sulfate (0.6 g). Insoluble materials were removed by filtration, and the solvent in the filtrate was distilled off by an evaporator to give a pale-yellow liquid (hereinafter to be referred to as "di-PZ4C2 form") (1.0 g).

<$^1$H-NMR Spectrum (600 MHz, CDCl$_3$)>

The analysis results of $^1$H-NMR spectrum of the obtained compound, di-PZ4C2 form, are shown below.

δ2.40-2.66 ppm (m, HO—CH$_2$—C$\underline{H}_2$—N—C$\underline{H}_2$—CH$_2$—N—, 20H), δ2.67-2.72 ppm (m, —N—CH$_2$—C$\underline{H}_2$—S—, 4H), 2.74-2.85 ppm (m, $\underline{H}$O—CH$_2$—, —N—C$\underline{H}_2$—CH$_2$—S—, 6H), 3.60-3.65 ppm (t, HO—C$\underline{H}_2$—CH$_2$—, 4H)

<Acylation>

The di-PZ4C2 form (3.0 g, 8 mmol) and D-α-tocopherol succinate (8.4 g, manufactured by SIGMA-ALDRICH) (16 mmol) were dissolved in chloroform (45 mL) at 20-25° C. Thereafter, 4-dimethylaminopyridine (0.4 g, manufactured by KOEI CHEMICAL CO., LTD.) (3 mmol) and EDC (4.6 g, manufactured by Tokyo Chemical Industry Co., Ltd.) (24 mmol) were added and the mixture was reacted at 30° C. for 4 hr. The disappearance of the spot of D-α-tocopherol succinate was confirmed by TLC analysis (eluent: chloroform/methanol=9/1(v/v), phosphoric acid copper sulfate color development), and the reaction was completed. The reaction solvent was distilled off by an evaporator, and hexane (200 mL) was added. Thereafter, acetonitrile (100 mL) was added, and the mixture was stirred for 5 min. After standing for 10 min, the hexane layer was recovered, and the solvent was distilled off by an evaporator to give a pale-yellow liquid (10.7 g). The liquid (9.0 g) was purified by silica gel column chromatography (eluent: chloroform/methanol=99/1-98/2(v/v)) to give the object product TS-PZ4C2 (5.7 g).

<$^1$H-NMR Spectrum (600 MHz, CDCl$_3$)>

The analysis results of $^1$H-NMR spectrum of the obtained compound, TS-PZ4C2, are shown below.

δ0.83-0.88 ppm (m, (C$\underline{H}_3$)$_2$CH—(CH$_2$)$_3$—(C$\underline{H}_3$)CH—(CH$_2$)$_3$—(CH$_3$)CH—, 24H), δ1.03-1.82 ppm (m, (CH$_3$)$_2$C$\underline{H}$—(C$\underline{H}_2$)$_3$—(CH$_3$)C$\underline{H}$—(C$\underline{H}_2$)$_3$—(CH$_3$)C$\underline{H}$—(C$\underline{H}_2$)$_3$—(C$\underline{H}_3$)C—, —C—C$\underline{H}_2$—CH$_2$—C—C—O—, 52H), δ1.95-2.09 ppm (m, Ar—C$\underline{H}_3$, 18H), δ2.40-2.60 ppm (m, —N—C$\underline{H}_2$—C$\underline{H}_2$—N—, —C—CH$_2$—C$\underline{H}_2$—C—C—O—, 20H), δ2.61-2.68 ppm (m, —O—CH$_2$—C$\underline{H}_2$—N—, —N—C$\underline{H}_2$—C$\underline{H}_2$—S—, 8H), δ2.75-2.84 ppm (m, Ar—O—C(O)—C$\underline{H}_2$—, —N—C$\underline{H}_2$—CH$_2$—S—, 8H), δ2.91-2.95 ppm (m, Ar—O—C(O)—CH$_2$—C$\underline{H}_2$—, 4H), δ4.21-4.25 ppm (t, —C(O)—C$\underline{H}_2$—CH$_2$—N—, 4H)

[Reference Example 2] Synthesis of L-PZ4C2

<Acylation>

The di-PZ4C2 form (2.5 g, 7 mmol) and linoleic acid (3.7 g, manufactured by NOF CORPORATION) (13 mmol) were dissolved in chloroform (25 mL) at 20-25° C. Thereafter, 4-dimethylaminopyridine (0.3 g, 3 mmol) and EDC (3.8 g, 20 mmol) were added and the mixture was reacted at 30° C. for 4 hr. The disappearance of the spot of linoleic acid was confirmed by TLC analysis (eluent: chloroform/methanol=9/1(v/v), phosphoric acid copper sulfate color development), and the reaction was completed. The reaction solvent was distilled off by an evaporator, and hexane (57 mL) was added. Thereafter, acetonitrile (24 mL) was added, and the mixture was stirred for 5 min. After standing for 10 min, the hexane layer was recovered, and the solvent was distilled off by an evaporator to give a pale-yellow liquid (4.9 g). The liquid (4.9 g) was purified by silica gel column chromatography (eluent: chloroform/methanol=99/1-97/3(v/v)) to give the object product L-PZ4C2 (3.1 g).

<¹H-NMR Spectrum (600 MHz, CDCl₃)>

The analysis results of ¹H-NMR spectrum of the obtained compound, L-PZ4C2, are shown below.

δ0.87-0.91 ppm (t, (C<u>H</u>₃—(CH₂)₃—CH₂—, 6H), δ1.25-1.38 ppm (m, CH₃—(C<u>H</u>₂)₃—CH₂—, —(C<u>H</u>₂)₄—CH₂—CH₂—C(O)—, 28H), δ1.58-1.63 ppm (m, —(CH₂)₄—C<u>H</u>₂—CH₂—C(O)—, 4H), δ2.00-2.07 ppm (m, —C<u>H</u>₂—CH=CH—CH₂—CH=CH—C<u>H</u>₂—, 8H), δ2.30-2.32 ppm (t, —(CH₂)₄—CH₂—C<u>H</u>₂—C(O)—, 4H), δ2.50-2.70 ppm (m, —N—C<u>H</u>₂—C<u>H</u>₂—N—, —N—CH₂—C<u>H</u>₂—S—, —O—CH₂—C<u>H</u>₂—N—, 24H), δ2.75-2.84 ppm (m, —CH=CH—C<u>H</u>₂—CH=CH—, —N—C<u>H</u>₂—CH₂—S—, 8H), δ4.18-4.21 ppm (t, —O—C<u>H</u>₂—CH₂—N—, 4H), δ5.30-5.41 ppm (m, —CH₂—C<u>H</u>=C<u>H</u>—CH₂—C<u>H</u>=C<u>H</u>—CH₂—, 8H)

[Example 6] Synthesis of O-PZ4C2

The di-PZ4C2 form (0.8 g, 2 mmol) and oleic acid (1.2 g, manufactured by NOF CORPORATION) (4 mmol) were dissolved in chloroform (8 mL) at 20-25° C. Thereafter, 4-dimethylaminopyridine (0.1 g, 1 mmol) and EDC (1.2 g, 6 mmol) were added and the mixture was reacted at 30° C. for 3 hr. The disappearance of the spot of oleic acid was confirmed by TLC analysis (eluent: chloroform/methanol=9/1(v/v), phosphoric acid copper sulfate color development), and the reaction was completed. The reaction solvent was distilled off by an evaporator, and hexane (12 mL) was added. Thereafter, acetonitrile (5 mL) was added, and the mixture was stirred for 5 min. After standing for 10 min, the hexane layer was recovered, and the solvent was distilled off by an evaporator to give a pale-yellow liquid (1.8 g). The liquid (1.7 g) was purified by silica gel column chromatography (eluent: chloroform/methanol=99/1-97/3(v/v)) to give the object product, O-PZ4C2 (1.1 g).

<¹H-NMR Spectrum (600 MHz, CDCl₃)>

The analysis results of ¹H-NMR spectrum of the obtained compound, O-PZ4C2, are shown below.

δ0.86-0.90 ppm (t, (C<u>H</u>₃—(CH₂)₆—CH₂—, 6H), δ1.25-1.34 ppm (m, CH₃—(C<u>H</u>₂)₆—CH₂—, —CH₂—(C<u>H</u>₂)₄—CH₂—CH₂—C(O)—, 40H), δ1.58-1.64 ppm (m, —CH₂—(CH₂)₄—C<u>H</u>₂—CH₂—C(O)—, 4H), δ1.99-2.03 ppm (m, —C<u>H</u>₂—CH=CH—C<u>H</u>₂—, 8H), δ2.28-2.32 ppm (m, —CH₂—(CH₂)₄—CH₂—C<u>H</u>₂—C(O)—, 4H), δ2.45-2.70 ppm (m, —N—C<u>H</u>₂—C<u>H</u>₂—N—, —O—CH₂—C<u>H</u>₂—N—, —N—CH₂—C<u>H</u>₂—S—, 24H), δ2.80-2.85 ppm (m, —N—C<u>H</u>₂—CH₂—S—, 4H), δ4.18-4.21 ppm (t, —O—C<u>H</u>₂—CH₂—N—, 4H), δ5.13-5.38 ppm (m, —CH₂—C<u>H</u>=C<u>H</u>—CH₂—, 4H)

[Reference Example 3] Synthesis of 4-Methylumbelliferone Cholesterol Hemisuccinate (4 MU-CHEMS)

Figure 22:
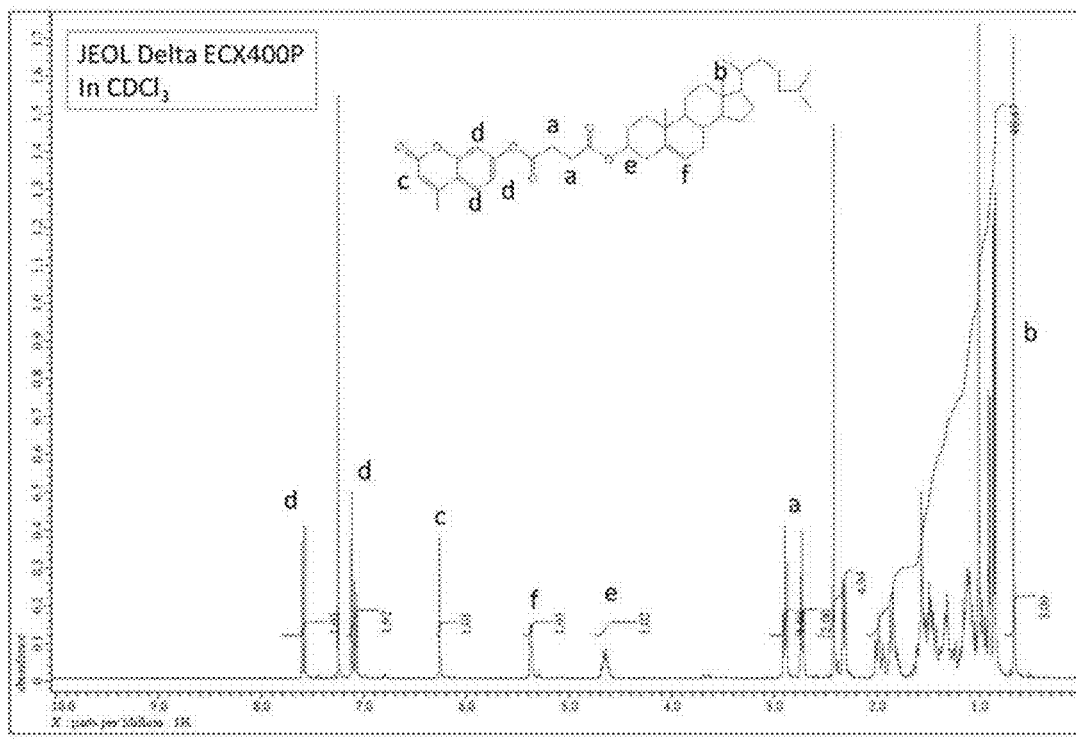
FIG. 22 shows analysis results of $^1$H-NMR spectrum of 4-methylumbelliferone cholesterol hemisuccinate.

The reaction was performed in argon. In an eggplant flask were added cholesteryl hemisuccinate (CHEMS) (2.43 g, 5 mmol), 4-methylumbelliferone (1.06 mg, 6 mmol), and anhydrous DMF (20 mL). Furthermore, N,N-Dimethyl-4-aminopyridine (DMAP) (61.1 mg, 0.5 mmol) was added, N,N-Diisopropylethylamine (DIPEA) (1.22 mL, 7 mmol) and 1-(3-Dimethylaminopropyl)-3-ethylcarbodiimide hydrochloride (EDCl) (1.15 g, 6 mmol) were added, and the mixture was reacted at room temperature overnight. The disappearance of the materials was confirmed by thin layer chromatography (TLC), and the mixture was purified by silica gel column chromatography. After drying, the objective substance 4-methylumbelliferone cholesterol hemisuccinate was obtained. The analysis results of ¹H-NMR spectrum of the obtained 4-methylumbelliferone cholesterol hemisuccinate are shown in FIG. 22, and the structural formula is shown below.

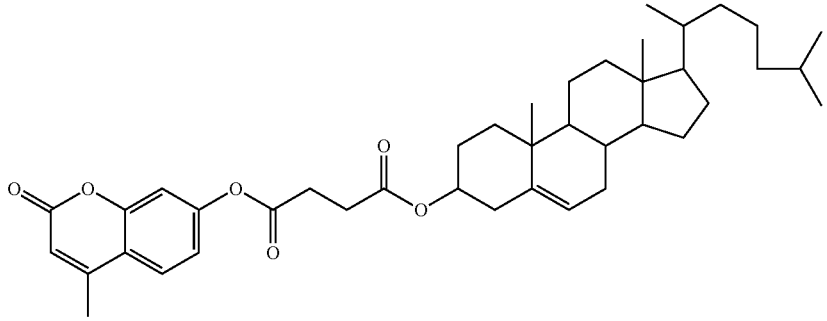 [SMILES: Cc1cc(=O)oc2cc(OC(=O)CCC(=O)OC3CCC4(C)C(=CCC5C4CCC4(C)C(C(C)CCCC(C)C)CCC54)C3)ccc12]

[Reference Example 4] Synthesis of Dexamethasone Cholesterol Hemisuccinate

Figure 23:
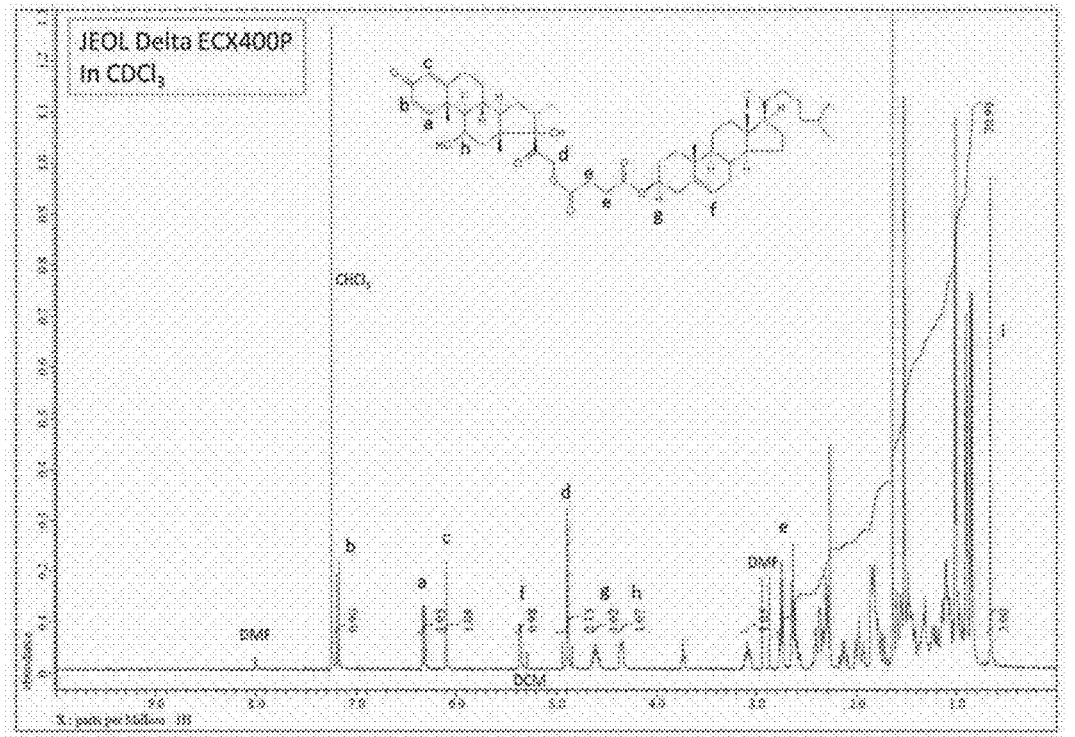
FIG. 23 shows analysis results of $^1$H-NMR spectrum of dexamethasone cholesterol hemisuccinate.

The reaction was performed in argon. In an eggplant flask were added cholesteryl hemisuccinate (CHEMS) (608.4 mg, 1.25 mmol), dexamethasone (588.7 mg, 1.5 mmol), and anhydrous DMF (20 mL). Furthermore, N,N-Dimethyl-4-aminopyridine (DMAP) (15.2 mg, 0.124 mmol) was added, N,N-Diisopropylethylamine (DIPEA) (0.305 mL, 1.75 mmol) and 1-(3-Dimethylaminopropyl)-3-ethylcarbodiimide hydrochloride (EDCl) (287.6 mg, 1.5 mmol) were added, and the mixture was reacted at room temperature overnight. The disappearance of the materials was confirmed by thin layer chromatography (TLC), and the mixture was purified by silica gel column chromatography. After drying, the objective substance dexamethasone cholesterol hemisuccinate was obtained. The analysis results of ¹H-NMR spectrum of the obtained dexamethasone cholesterol hemisuccinate are shown in FIG. 23, and the structural formula is shown below.

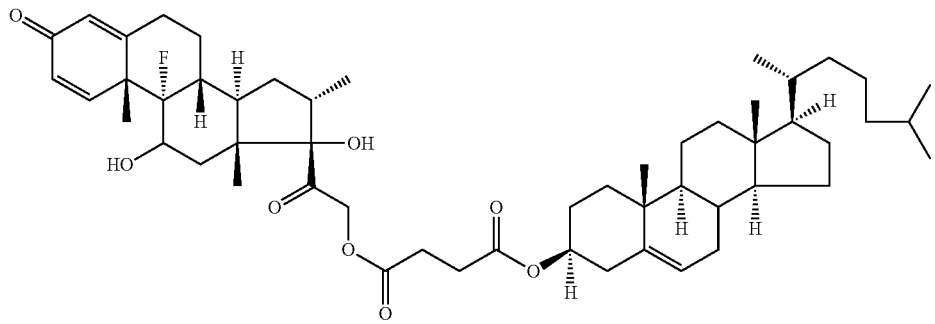

INDUSTRIAL APPLICABILITY

According to the O/W type emulsion of the present invention, a hardly water-soluble drug can be stably encapsulated therein. When the O/W type emulsion of the present invention encapsulating a hardly water-soluble drug is taken up by cells, the compound represented by the formula (I) is decomposed by the reductive environment in the cell to disintegrate the O/W type emulsion, whereby the hardly water-soluble drug contained therein is efficiently released in the cells. Therefore, the O/W type emulsion of the present invention is useful as a carrier for delivering a hardly water-soluble drug into cells. In addition, since the O/W type emulsion of the present invention has a volume median diameter of 100 nm or below, discharge from the spleen can be avoided, high retentivity in blood and high accumulation in the target tissue such as tumor and the like can be exhibited, and it is advantageous for delivering a hardly water-soluble drug to a target tissue in the body.

This application is based on a patent application No. 2015-200148 filed in Japan (filing date: Oct. 8, 2015), the contents of which are incorporated in full herein.

The invention claimed is:

1. An O/W type emulsion having a volume median diameter of not more than 100 nm and comprising a compound represented by the formula (1)

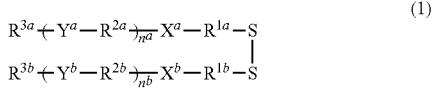

wherein $X^a$ and $X^b$ are each independently $X^1$, $X^2$ or 1,4-piperazinediyl group;

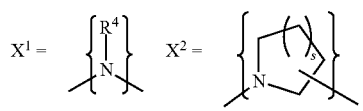

s is 1 or 2,
$R^4$ is an alkyl group having 1-6 carbon atoms,
$n^a$ and $n^b$ are each independently 0 or 1,
$R^{1a}$ and $R^{1b}$ are each independently an alkylene group having 1-6 carbon atoms,
$R^{2a}$ and $R^{2b}$ are each independently an alkylene group having 1-6 carbon atoms,
$Y^a$ and $Y^b$ are each independently an ester bond, an amide bond, a carbamate bond, an ether bond or a urea bond,
$R^{3a}$ and $R^{3b}$ are each independently a sterol residue, a liposoluble vitamin residue or an aliphatic hydrocarbon group having 12-23 carbon atoms,
the sterol residue is a residue derived from cholesterol, cholestanol, stigmasterol, β-sitosterol, lanosterol, ergosterol, cholesterol hemisuccinate, or cholesterol hemiglutarate, and
the liposoluble vitamin residue is a residue derived from retinoic acid, retinol, retinal, ergosterol, 7-dehydrocholesterol, calciferol, cholecalciferol, dihydroergocalciferol, dihydrotachysterol, tocopherol, tocotrienol, tocopherol hemisuccinate, or tocopherol hemiglutarate, and
encapsulating a drug having a water/octanol distribution coefficient Log Pow of not less than 5.

2. The O/W type emulsion according to claim 1, wherein the volume median diameter is 30-50 nm.

3. The O/W type emulsion according to claim 1, further comprising at least one selected from the group consisting of phospholipid, cholesterol and PEG lipid.

4. The O/W type emulsion according to claim 1, wherein the drug is 4-methylumbelliferone cholesterol hemisuccinate or dexamethasone cholesterol hemisuccinate.

5. A method for delivering a drug having a water/octanol distribution coefficient Log Pow of not less than 5 into a cell, comprising contacting the O/W type emulsion according to claim 1 with the cell.

6. The method according to claim 5, wherein the O/W type emulsion is brought into contact with the cell in vitro.

7. The method according to claim 5, wherein the O/W type emulsion is brought into contact with the cell by administration to a body.

8. The O/W type emulsion according to claim 2, wherein the drug is 4-methylumbelliferone cholesterol hemisuccinate or dexamethasone cholesterol hemisuccinate.

9. The O/W type emulsion according to claim 2, further comprising at least one selected from the group consisting of phospholipid, cholesterol and PEG lipid.

10. The O/W type emulsion according to claim 9, wherein the drug is 4-methylumbelliferone cholesterol hemisuccinate or dexamethasone cholesterol hemisuccinate.

* * * * *